United States Patent
Heo et al.

(10) Patent No.: US 8,822,722 B2
(45) Date of Patent: Sep. 2, 2014

(54) FLUORESCENT HYDROGEL AND METHOD FOR PRODUCING THE SAME, AND SENSOR FOR MEASURING SACCHARIDES USING THE SAME

(75) Inventors: Yun-Jung Heo, Tokyo (JP); Hideaki Shibata, Sagamihara (JP); Tetsuro Kawanishi, Isehara (JP); Shoji Takeuchi, Tokyo (JP); Yukiko Matsunaga, Tokyo (JP); Teru Okitsu, Komae (JP)

(73) Assignees: Terumo Kabushiki Kaisha, Shibuya-Ku, Tokyo (JP); The University of Tokyo, Bunkyo-Ku, Tokyo (JP)

( * ) Notice: Subject to any disclaimer, the term of this patent is extended or adjusted under 35 U.S.C. 154(b) by 0 days.

(21) Appl. No.: 13/877,004

(22) PCT Filed: Sep. 7, 2011

(86) PCT No.: PCT/JP2011/070389
§ 371 (c)(1),
(2), (4) Date: May 31, 2013

(87) PCT Pub. No.: WO2012/043177
PCT Pub. Date: Apr. 5, 2012

(65) Prior Publication Data
US 2013/0267800 A1  Oct. 10, 2013

(30) Foreign Application Priority Data
Sep. 30, 2010  (JP) .................................. 2010-222363

(51) Int. Cl.
*C07F 5/02* (2006.01)
*C08F 222/00* (2006.01)
(Continued)

(52) U.S. Cl.
CPC .......... *A61B 5/0071* (2013.01); *G01N 21/6428* (2013.01); *C08F 220/54* (2013.01); *G01N 2021/7786* (2013.01); *A61B 5/14532* (2013.01); *C08F 220/36* (2013.01); *Y10S 436/80* (2013.01)
USPC ............... 564/8; 560/221; 600/316; 436/800; 427/2.21; 252/301.16

(58) Field of Classification Search
USPC ............... 564/8; 560/221; 600/316; 436/800; 427/2.213; 252/301.16
See application file for complete search history.

(56) References Cited

U.S. PATENT DOCUMENTS 5,503,770 A  4/1996  James et al.
6,319,540 B1  11/2001  Van Antwerp et al.
(Continued)

FOREIGN PATENT DOCUMENTS

JP    8-053467 A    2/1996
JP    2004-506069 A    2/2004
(Continued)

OTHER PUBLICATIONS

International Search Report (PCT/ISA/210) issued on Dec. 13, 2011, by the Japanese Patent Office as the International Searching Authority for International Application No. PCT/JP2011/070389.
(Continued)

*Primary Examiner* — Sikarl Witherspoon
(74) *Attorney, Agent, or Firm* — Buchanan Ingersoll & Rooney PC

(57) ABSTRACT

To provide a fluorescent hydrogel having superior detectability of saccharides such as glucose and minimal invasiveness, a method for producing the same, and a sensor for measuring saccharides using the same. A florescent hydrogel having a structure represented by the following chemical formula 1, a method for producing the same, and a sensor for measuring saccharides using the same.

[Chemical Formula 1]

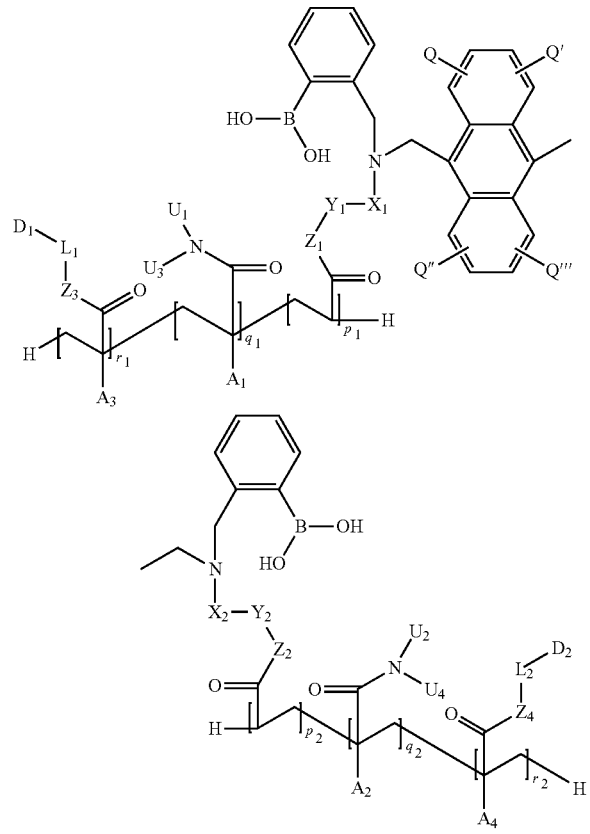

11 Claims, 10 Drawing Sheets

(51) Int. Cl.
*G01N 33/53* (2006.01)
*C09K 11/06* (2006.01)
*A61B 5/145* (2006.01)
*G01N 21/64* (2006.01)
*C08F 220/54* (2006.01)
*A61B 5/00* (2006.01)
*C08F 220/36* (2006.01)
*G01N 21/77* (2006.01)

(56) References Cited

U.S. PATENT DOCUMENTS

| | | | | |
|---|---|---|---|---|
| 7,078,554 | B2* | 7/2006 | Daniloff et al. | 558/288 |
| 7,388,110 | B2* | 6/2008 | Ochiai et al. | 564/8 |
| 7,851,225 | B2* | 12/2010 | Colvin et al. | 436/95 |
| 7,873,398 | B2* | 1/2011 | Ochiai et al. | 600/317 |
| 2006/0020182 | A1 | 1/2006 | Ochiai et al. | |
| 2008/0021236 | A1 | 1/2008 | Ochiai et al. | |
| 2008/0319288 | A1 | 12/2008 | Ochiai et al. | |

FOREIGN PATENT DOCUMENTS

| | | |
|---|---|---|
| JP | 2006-104140 A | 4/2006 |
| JP | 2006-111719 A | 4/2006 |
| JP | 2010-209339 A | 9/2010 |
| WO | WO 02/12251 A1 | 2/2002 |

OTHER PUBLICATIONS

Written Opinion (PCT/ISA/237) issued on Dec. 13, 2011, by the Japanese Patent Office as the International Searching Authority for International Application No. PCT/JP2011/070389.

* cited by examiner

FIG.8 ( a )
FIG.8 ( b )
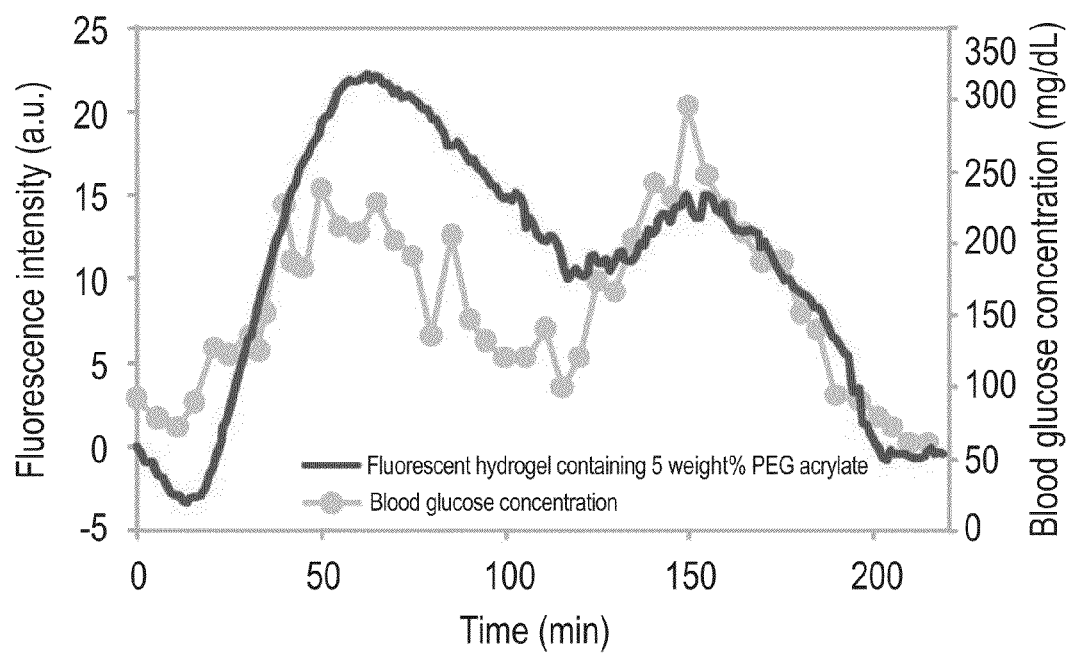

FIG.9 ( a )
FIG.9 ( b )
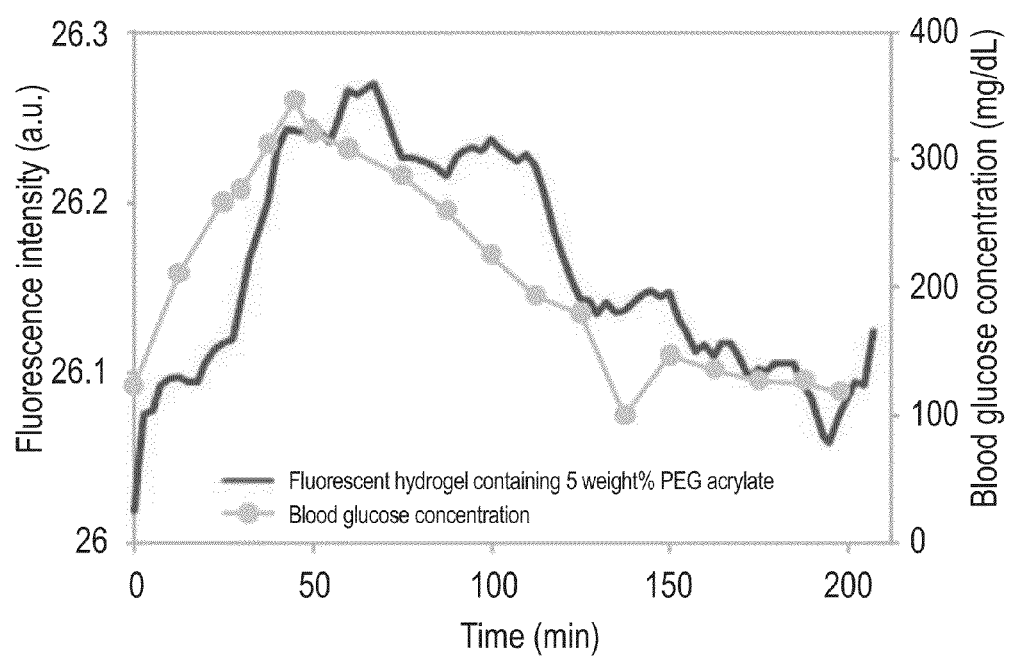

FIG.10 ( a )
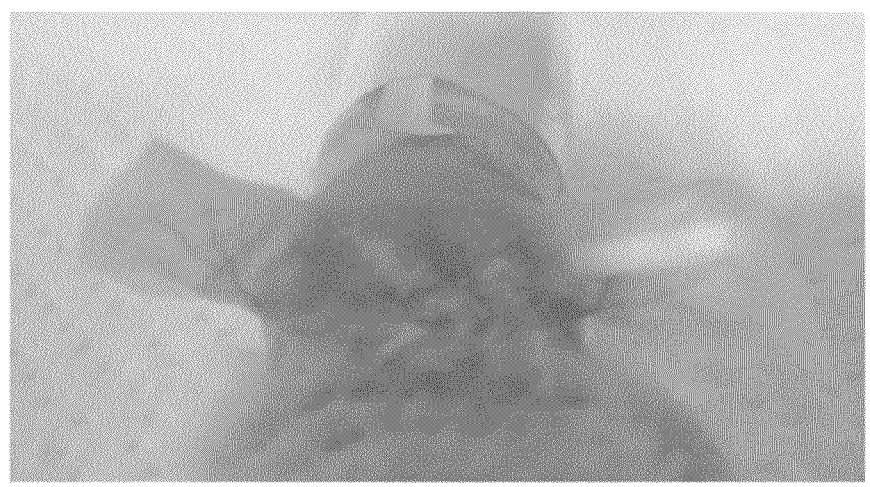
FIG.10 ( b )
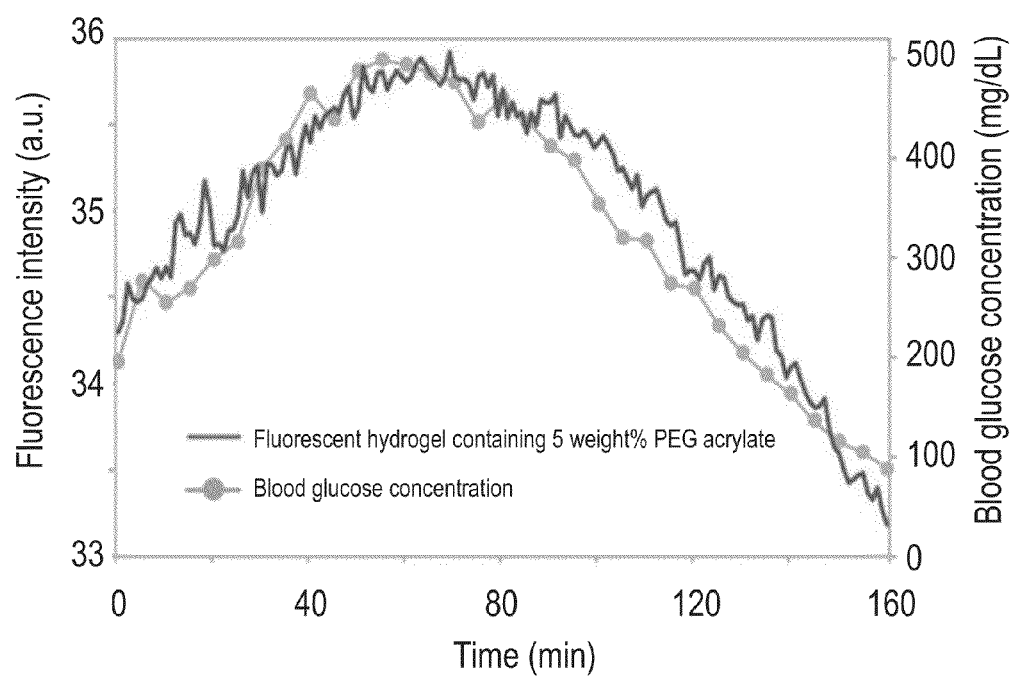

FLUORESCENT HYDROGEL AND METHOD FOR PRODUCING THE SAME, AND SENSOR FOR MEASURING SACCHARIDES USING THE SAME

TECHNICAL FIELD

The present invention relates to a fluorescent hydrogel and a method for producing the same, and a sensor for measuring saccharides using the same.

BACKGROUND ART

An implantable sensor is useful for, in various diseases, e.g. a follow-up on the state of disease and monitoring therapeutic effects, and is one of the fields which have been actively studied in recent years. In particular in the treatment of diabetes, blood glucose control by continuous blood glucose measurements is said to contribute to the delayed progression of the state of disease and a decrease in development of complications.

Under the present circumstances, most of the diabetics collect a blood sample by puncturing a finger or the like, supply the sample to a blood glucose meter, and read a measured value to manage blood glucose by themselves. Such method, however, has problems in terms of distress of patients and simplicity, and the measurements are limited to a few times a day. Under the present circumstances, it is difficult to understand the trend and tendency of changes in blood glucose level by frequent measurements. For such reasons, it is believed that the usefulness of an implantable continuous blood glucose meter is high.

Meanwhile, technology for continuously measuring glucose concentrations in a living body has been developed for a long time. For example, there is technology in which glucose concentrations are measured by changes in the amount of fluorescence using a substance which emits fluorescence by a reversible reaction with glucose. As fluorescent substances of this type, Patent Literature 1 discloses a fluorescent compound having a fluorescent group of atoms, at least one phenylboronic acid region and at least one amine nitrogen, and a molecular structure in which the amine nitrogen is located near the phenylboronic acid region and intramolecularly binds to the phenylboronic acid. In addition, Patent Literature 2 discloses, as an indicator high molecule to detect the concentration of a sample in an aqueous environment, a copolymer of a hydrophilic monomer and an indicator monomer which has an excimer-forming polycyclic aromatic hydrocarbon such as an anthracene boronic acid ester derivative. Further, Patent Literature 3 discloses a method in which a fluorescent substance is directly immobilized on a solid phase such as a plastic film as a fluorescence sensor.

The sensor substances described in the above Patent Literatures 1 to 3 are, however, in the shape of films and the shape of sheets, and when the substances are implanted to use in a body, there is a problem of high invasiveness. For such problem, Patent Literature 4 suggests a sensor for measuring saccharides, in which a fluorescent sensor substance is immobilized on a base material such as a (meth)acrylamide film using a silane coupling agent and the like.

CITATION LIST

Patent Literature

Patent Literature 1: Japanese Patent Application Laid-Open (JP-A) No. H08-53467 A (U.S. Pat. No. 5,503,770)

Patent Literature 2: Japanese Patent Application National Publication (Laid-Open) No. 2004-506069 (WO2002/012251)
Patent Literature 3: U.S. Pat. No. 6,319,540
Patent Literature 4: JP-A No. 2006-104140 A

SUMMARY OF INVENTION

Technical Problem

The sensor for measuring saccharides described in the above Patent Literature 4, however, requires skin incisions for implantation in and removal from a body, and thus there is room for improvement in inhibiting invasion as much as possible.

Therefore, an object of the present invention is to provide a fluorescent hydrogel, which has superior detectability of saccharides such as glucose, and is easily implanted in and removed from a body with minimal invasiveness, and a method for producing the same, and a sensor for measuring saccharides using the same.

Solution to Problem

As a result of a long series of intensive research, the present inventors found that a fluorescent hydrogel having a polyalkylene oxide structure has superior detectability of saccharides such as glucose, and can be implanted in a body and removed from the body with lower invasiveness, thereby completing the present invention.

Advantageous Effects of Invention

A fluorescent hydrogel by the present invention and a sensor for measuring saccharides using the same have superior detectability of saccharides in body fluid, and can be implanted in a body and removed from the body with minimal invasiveness.

BRIEF DESCRIPTION OF THE DRAWINGS

FIG. 8(*a*) is a photograph when implanting the fluorescent hydrogel obtained in Example 2 in a mouse ear, and FIG. 8(*b*) is a graph showing the relationship between changes in the blood glucose level of the mouse and changes in the fluorescence intensity of the fluorescent hydrogel.

FIG. 9(*a*) is a photograph of a mouse after 72 days from implantation of the fluorescent hydrogel in an ear, and FIG. 9(*b*) is a graph showing evaluation results of the relationship between changes in the blood glucose level of the mouse and changes in the fluorescence intensity of the fluorescent hydrogel, which has been implanted, after 72 days from implantation of the fluorescent hydrogel.

FIG. 10(*a*) is a photograph of a mouse after 140 days from implantation of the fluorescent hydrogel in an ear, and FIG. 10(*b*) is a graph showing evaluation results of the relationship between changes in the blood glucose level of the mouse and changes in the fluorescence intensity of the fluorescent hydrogel, which has been implanted, after 140 days from implantation of the fluorescent hydrogel.

DESCRIPTION OF EMBODIMENTS

Figure 1:
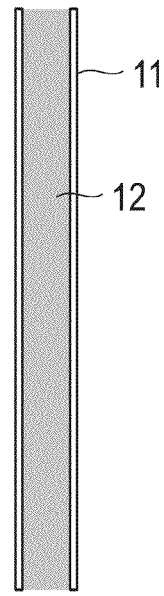
FIG. 1 is a schematic diagram showing an aqueous solution column 12 filled in a tube 11.

The first of the present invention is a fluorescent hydrogel having a structure represented by the following chemical formula 1.

[Chem. 1]

[Chemical Formula 1]

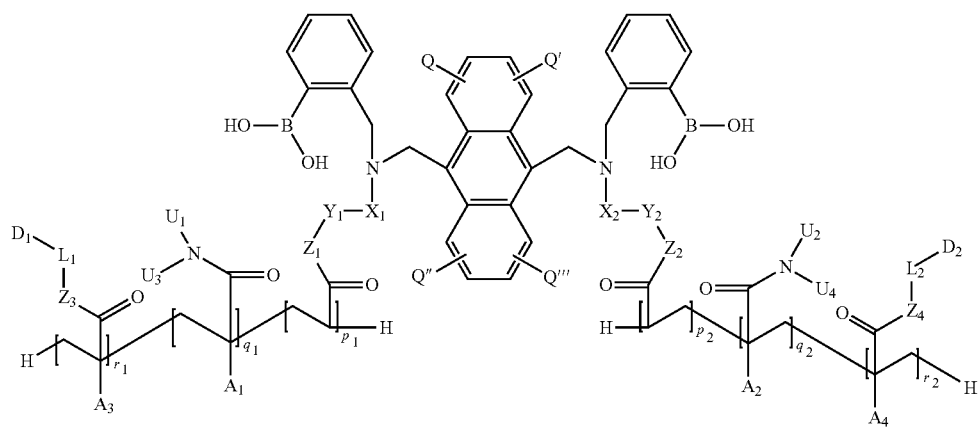

In the chemical formula 1, $X_1$ and $X_2$, which may be the same or different, are straight or branched C1-30 alkylene which may include at least one substituent selected from the group consisting of —COO—, —OCO—, —CH$_2$NR—, —NR—, —NRCO—, —CONR—, —SO$_2$NR—, —NRSO$_2$—, —O—, —S—, —SS—, —NRCOO—, —OCONR— and —CO—, in this case, R is a hydrogen atom, or substituted or unsubstituted straight or branched C1-10 alkyl.

Specific examples of straight or branched C1-30 alkylene include, for example, methylene, ethylene, propylene, isopropylene, butylene, isobutylene, sec-butylene, tert-butylene, pentylene, isopentylene, neopentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, hexacosylene, heptacosylene, octacosylene, nonacosylene or triacontylene, and the like. C3-12 alkylene is preferred, and propylene, hexylene or octylene is more preferred.

The substituents contained in the alkylene may be located at the end of the alkylene, and located in the interior of the alkylene. A preferred substituent is —NRCO— or —CONR—. R is a hydrogen atom, or straight or branched C1-10 alkyl, and more preferably a hydrogen atom.

Specific examples of straight or branched C1-10 alkyl which can be used as R include, for example, methyl, ethyl, n-propyl, isopropyl, n-butyl, isobutyl, sec-butyl, tert-butyl, n-pentyl, iso-amyl, tert-pentyl, neopentyl, n-hexyl, 3-methylpentan-2-yl, 3-methylpentan-3-yl, 4-methylpentyl, 4-methylpentan-2-yl, 1,3-dimethylbutyl, 3,3-dimethylbutyl, 3,3-dimethylbutan-2-yl, n-heptyl, 1-methylhexyl, 3-methylhexyl, 4-methylhexyl, 5-methylhexyl, 1-ethylpentyl, 1-(n-propyl)butyl, 1,1-dimethylpentyl, 1,4-dimethylpentyl, 1,1-diethylpropyl, 1,3,3-trimethylbutyl, 1-ethyl-2,2-dimethylpropyl, n-octyl, 2-ethylhexyl, 2-methylhexan-2-yl, 2,4-dimethylpentan-3-yl, 1,1-dimethylpentan-1-yl, 2,2-dimethylhexan-3-yl, 2,3-dimethylhexan-2-yl, 2,5-dimethylhexan-2-yl, 2,5-dimethylhexan-3-yl, 3,4-dimethylhexan-3-yl, 3,5-dimethylhexan-3-yl, 1-methylheptyl, 2-methylheptyl, 5-methylheptyl, 2-methylheptan-2-yl, 3-methylheptan-3-yl, 4-methylheptan-3-yl, 4-methylheptan-4-yl, 1-ethylhexyl, 2-ethylhexyl, 1-propylpentyl, 2-propylpentyl, 1,1-dimethylhexyl, 1,4-dimethylhexyl, 1,5-dimethylhexyl, 1-ethyl-1-methylpentyl, 1-ethyl-4-methylpentyl, 1,1,4-trimethylpentyl, 2,4,4-trimethylpentyl, 1-isopropyl-1,2-dimethylpropyl, 1,1,3,3-tetramethylbutyl, n-nonyl, 1-methyloctyl, 6-methyloctyl, 1-ethylheptyl, 1-(n-butyl)pentyl, 4-methyl-1-(n-propyl)pentyl, 1,5,5-trimethylhexyl, 1,1,5-trimethylhexyl, 2-methyloctan-3-yl, n-decyl, 1-methylnonyl, 1-ethyloctyl, 1-(n-butyl)hexyl, 1,1-dimethyloctyl or 3,7-dimethyloctyl, and the like. Straight or branched C1-5 alkyl is more preferred.

In the chemical formula 1, $Z_1$, $Z_2$, $Z_3$ and $Z_4$, which may be the same or different, are —O— or —NR'—, in this case, R' is a hydrogen atom, or substituted or unsubstituted C1-10 alkyl. $Z_1$ and $Z_2$ are more preferably —O—.

Specific examples of straight or branched C1-10 alkyl which can be used as R' are the same as above, and thus the explanation is omitted here. Straight or branched C1-5 alkyl is more preferred.

Q, Q', Q" and Q''', which may be the same or different, are hydrogen atoms, hydroxy, substituted or unsubstituted straight or branched C1-10 alkyl, C2-11 acyl, substituted or unsubstituted straight or branched C1-10 alkoxy, halogen atom-containing groups, carboxy, carboxylic acid ester, carboxylic acid amide, cyano, nitro, amino or C1-10 alkylamino.

Specific examples of straight or branched C1-10 alkyl are the same as above, and thus the explanation is omitted here.

It is preferred that C2-11 acyl be a group represented by the following chemical formula 2.

[Chem. 2]

[Chemical Formula 2]

In the chemical formula 2, L is substituted or unsubstituted straight or branched C1-10 alkyl.

Examples of C2-11 acyl include, for example, acetyl, propionyl, butyryl, isobutyryl, valeryl or isovaleryl, and the like. The number of carbons in alkyl of L in the chemical formula 2 is preferably 1 to 4 and more preferably 1 (i.e. acetyl). The effect of expanding the gap between the excitation wavelength and the maximum fluorescence wavelength is obtained by introducing acyl into the anthracene residue.

Examples of straight or branched C1-10 alkoxy include, for example, methoxy, ethoxy, n-propoxy, isopropoxy, n-butoxy, isobutoxy, sec-butoxy, tert-butoxy, n-pentyloxy, isopentyloxy, neopentyloxy, 1,2-dimethyl-propoxy, n-hexyloxy, 3-methylpentan-2-yloxy, 3-methylpentan-3-yloxy, 4-methylpentyloxy, 4-methylpentan-2-yloxy, 1,3-dimethylbutyloxy, 3,3-dimethylbutyloxy, 3,3-dimethylbutan-2-yloxy, n-heptyloxy, 1-methylhexyloxy, 3-methylhexyloxy, 4-methylhexyloxy, 5-methylhexyloxy, 1-ethylpentyloxy, 1-(n-propyl)butyloxy, 1,1-dimethylpentyloxy, 1,4-dimethylpentyloxy, 1,1-diethylpropyloxy, 1,3,3-trimethylbutyloxy, 1-ethyl-2,2-dimethylpropyloxy, n-octyloxy, 2-ethylhexyloxy, 2-methylhexan-2-yloxy, 2,4-dimethylpentan-3-yloxy, 1,1-dimethylpentan-1-yloxy, 2,2-dimethylhexan-3-yloxy, 2,3-dimethylhexan-2-yloxy, 2,5-dimethylhexan-2-yloxyoxy, 2,5-dimethylhexan-3-yloxy, 3,4-dimethylhexan-3-yloxy, 3,5-dimethylhexan-3-yloxy, 1-methylheptyloxy, 2-methylheptyloxy, 5-methylheptyloxy, 2-methylheptan-2-yloxy, 3-methylheptan-3-yloxy, 4-methylheptan-3-yloxy, 4-methylheptan-4-yloxy, 1-ethylhexyloxy, 2-ethylhexyloxy, 1-propylpentyloxy, 2-propylpentyloxy, 1,1-dimethylhexyloxy, 1,4-dimethylhexyloxy, 1,5-dimethylhexyloxy, 1-ethyl-1-methylpentyloxy, 1-ethyl-4-methylpentyloxy, 1,1,4-trimethylpentyloxy, 2,4,4-trimethylpentyloxy, 1-isopropyl-1,2-dimethylpropyloxy, 1,1,3,3-tetramethylbutyloxy, n-nonyloxy, 1-methyloctyloxy, 6-methyloctyloxy, 1-ethylheptyloxy, 1-(n-butyl)pentyloxy, 4-methyl-1-(n-propyl)pentyloxy, 1,5,5-trimethylhexyloxy, 1,1,5-trimethylhexyloxy, 2-methyloctan-3-yloxy, n-decyloxy, 1-methylnonyloxy, 1-ethyloctyloxy, 1-(n-butyl)hexyloxy, 1,1-dimethyloctyloxy or 3,7-dimethyloctyloxy, and the like.

Examples of halogen atom-containing groups include, for example, F—, Cl—, Br—, I— or OI— (iodoxy), and the like.

Examples of C1-10 alkylamino include e.g. methylamino, ethylamino, n-propylamino, isopropylamino, n-butylamino, n-pentylamino, n-hexylamino, n-octylamino, n-decylamino or n-isoamylamino, and the like.

In addition, at least one of Q and Q', and Q" and Q'" may join together to form an aromatic ring or a heterocycle. Examples of the aromatic rings include, for example, a benzene ring. Examples of the heterocycles include, for example, a pyrazole ring, a pyrrole ring, a furan ring, a thiophene ring, an imidazole ring, a thiazole ring, an isothiazole ring, an oxazole ring, an isoxazole ring, a pyridine ring, a pyrazine ring, a pyrimidine ring, a pyridazine ring and the like.

The introduction of nitro, cyano or acyl into at least one of Q, Q', Q" and Q'" can contribute to a fluorescence red shift or expansion of the gap between the excitation wavelength peak and the fluorescence wavelength peak, and is preferred.

In the present invention, at least one of Q, Q', Q" and Q'" is preferably nitro, cyano or C2-11 acyl represented by the chemical formula 2, more preferably nitro, cyano or acetyl, and further preferably acetyl. In addition, one to three of Q, Q', Q" and Q'" are preferably substituted with the above substituents, more preferably one and two of them, and further preferably one of them.

$Y_1$ and $Y_2$, which may be the same or different, are divalent organic residues which may be substituted, or single bonds. It is preferred that $Y_1$ and $Y_2$ have hydrophilicity which can render a fluorescent monomer compound water-soluble. Here, hydrophilicity which can render a fluorescent monomer compound water-soluble means that the fluorescent monomer compound is dissolved in water in a concentration range required for polymerization thereof in the absence of an organic solvent and a solubilizing agent. Specific examples of groups used as $Y_1$ and $Y_2$ are, for example, amino, carbonyloxy, or a divalent organic residue having a hydrophilic group such as sulfonate group, nitro, amino, phosphate group or hydroxy, and a divalent organic residue having a hydrophilic bond such as an ether bond, an amide bond or an ester bond in its structure.

It is preferred that at least one of $Y_1$ and $Y_2$ contains a group represented by the following chemical formula 3 or the following chemical formula 4. In addition, at least one of $Y_1$ and $Y_2$ may contain both a group represented by the following chemical formula 3 and a group represented by the following chemical formula 4, in this case, the configuration of a group represented by the following chemical formula 3 and a group represented by the following chemical formula 4 may be a block form or a random form. Further, at least one of $Y_1$ and $Y_2$ may have other substituents and divalent organic residues described above.

[Chem. 3]

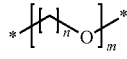

[Chemical Formula 3]

[Chem. 4]

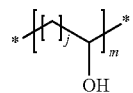

[Chemical Formula 4]

In the chemical formula 3 and the chemical formula 4, n is 2 to 5, preferably 2 to 4, and more preferably 2 or 3. In addition, j is 1 to 5, preferably 1 to 3, and more preferably 1. Further, m is 1 to 200, preferably 20 to 150, and more preferably 40 to 120. The * in the chemical formula 3 and the chemical formula 4 represents a binding point.

The molecular weight of the $Y_1$ and $Y_2$ moieties is preferably 500 to 10,000, and more preferably 1,000 to 5,000. The divalent organic residue represented by the chemical formula 3 or the chemical formula 4 can be formed, for example, by polymerizing an alkylene glycol such as ethylene glycol or propylene glycol, or vinyl alcohol.

$A_1$, $A_2$, $A_3$ and $A_4$, which may be the same or different, are hydrogen atoms or methyl.

$U_1$, $U_2$, $U_3$ and $U_4$, which may be the same or different, are hydrogen atoms, or substituted or unsubstituted straight or branched C1-10 alkyl.

$D_1$ and $D_2$, which may be the same or different, are groups represented by the following chemical formula 6.

[Chem. 5]

[Chemical Formula 6]

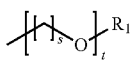

In the chemical formula 6, $R_1$ is a hydrogen atom, or straight or branched C1-10 alkyl, in this case, $R_1$ may form a bond with $L_1$, $L_2$, $Z_1$ or $Z_2$, to which $D_1$ and $D_2$ are not bound, s is an integer from 2 to 5, and t is an integer from 1 to 200.

In the chemical formula 6, s is preferably an integer from 2 to 4, and more preferably 2. Further, t is preferably an integer from 20 to 150, and more preferably an integer from 40 to 120.

The introduction of a group represented by the above chemical formula 6 (polyalkylene oxide structure), which group is hydrophilic, changes the peripheral environment and mobility of phenylboronic acid, which interacts with a substance to be detected, and contributes to e.g. an improvement in the sensitivity, accuracy and response speed of a fluorescent hydrogel to be ultimately obtained and the selectivity of saccharides, which are substances to be measured. In addition, a steric repulsion effect due to the structure represented by the above chemical formula 6 contributes to an improvement in the effect of inhibiting adsorption of biological components such as protein, for example, albumin and lipid.

$L_1$ and $L_2$, which may be the same or different, are groups selected from the group consisting of a single bond, —$U_5$—, —$U_5$—$NR_2$—, —$U_5$—O—, —$U_5$—S—, —$U_5$—SS—, —$U_5$—$NR_2$CO—, —$U_5$—$CONR_2$—, —$U_5$—OCO—, —$U_5$—COO—, a group represented by the following chemical formula 7, and a group represented by the following chemical formula 8,

[Chem. 6]

[Chemical Formula 7]

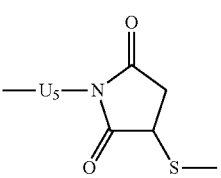

[Chem. 7]

[Chemical Formula 8]

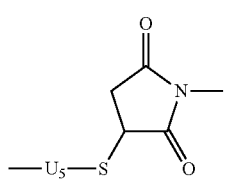

in this case, $U_5$ is substituted or unsubstituted straight or branched C1-10 alkylene, and $R_2$ is a hydrogen atom, or substituted or unsubstituted straight or branched C1-10 alkyl.

Specific examples of the above straight or branched C1-10 alkylene include, for example, methylene, ethylene, propylene, isopropylene, butylene, isobutylene, sec-butylene, tert-butylene, pentylene, isopentylene, neopentylene, hexylene, heptylene, octylene, nonylene or decylene, and the like. Preferred are propylene, butylene, pentylene, hexylene, heptylene, octylene, nonylene and decylene, and more preferred are hexylene, heptylene, octylene, nonylene and decylene.

The mention of "substituted or unsubstituted" in this description means substitution with substituents such as a fluorine atom; a chlorine atom; a bromine atom; cyano; nitro; hydroxy; straight or branched C1-10 alkyl; straight or branched C1-10 alkoxy; C6-30 aryl; C2-30 heteroaryl; and C5-20 cycloalkyl; or unsubstitution.

The molar ratio of $p_1$ and $q_1$ ($p_1$:$q_1$) and the molar ratio of $p_2$ and $q_2$ ($p_2$:$q_2$) are 1:50 to 1:6,000, preferably 1:50 to 1:4,000, and more preferably 1:100 to 1:2,000. When the proportion of a fluorescent monomer compound is higher than a molar ratio of 1:50, a degree of freedom may be lost due to the bulky of the fluorescent monomer compound, and there is a possibility that interactions with saccharides may decrease. On the contrary, when the proportion of a fluorescent monomer compound is lower than a molar ratio of 1:6,000, the absolute magnitude of the fluorescence intensity may not be secured.

The molar ratio of $p_1$ and $r_1$ ($p_1$:$r_1$) and the molar ratio of $p_2$ and $r_2$ ($p_2$:$r_2$) are 1:5 to 1:3,000, preferably 1:8 to 1:2,500, and more preferably 1:10 to 1:2,000. When the proportion of a fluorescent monomer compound is higher than a molar ratio of 1:5, a degree of freedom may be lost due to the bulky of the fluorescent monomer compound, and there is a possibility that interactions with saccharides may decrease. On the contrary, when the proportion of a fluorescent monomer compound is lower than a molar ratio of 1:3,000, the absolute magnitude of the fluorescence intensity may not be secured. In addition, $p_1$ and $p_2$ are preferably almost 1 to 30, and $q_1$ and $q_2$ are preferably almost 50 to 180,000. Also, $r_1$ and $r_2$ are preferably almost 5 to 90,000.

Methods for introducing a group represented by the above chemical formula 6 into a fluorescent hydrogel will be described in detail in the paragraph of the production method for a fluorescent hydrogel described below.

As described above, in the structure of the fluorescent hydrogel of the present invention, it is preferred that divalent organic residues, $Y_1$ and $Y_2$, have hydrophilicity. Thereby, concretely, the following effects are obtained. (1) Because a fluorescent monomer compound becomes water-soluble, a polymerization reaction can be efficiently carried out when forming a fluorescent hydrogel. (2) The introduction of hydrophilic chains changes the peripheral environment and mobility of phenylboronic acid, which interacts with a substance to be detected, and contribute to an improvement in sensitivity, accuracy and response speed and the selectivity of saccharides, which are substances to be measured. (3) The hydrophilic chains stabilize the overall structure of a fluorescent hydrogel. (4) Because reactions can be carried out only in water, polymerization can be carried out in a suspended state in an organic solvent.

The weight average molecular weight of a fluorescent hydrogel having a structure represented by the above chemical formula 1 is preferably 50,000 to 750,000 and more preferably 150,000 to 450,000 in terms of polyethylene oxide by gel permeation chromatography (GPC).

The shape of the fluorescent hydrogel of the present invention is not restricted, and may be any shape e.g. a spherical type, a cylindrical type, a prismatic type, a cubic type and a fibrous type, or hollow shapes thereof, or three-dimensional structures constructed using these, such as a woven fabric structure, a cylindrical structure, a tube and a spring structure. It is preferred that a suitable shape be selected depending on a method for implanting a fluorescent hydrogel and when detecting fluorescence.

The size of the fluorescent hydrogel by the present invention is not restricted, and preferably 10 to 2000 μm, and more preferably 100 to 1000 μm when implantation is carried out using an injector, a cannula or a catheter. In this description, a value measured by a stereoscopic microscope is used as its diameter.

In addition, it is preferred that the size of fluorescent hydrogels be almost equal in order that each fluorescent hydrogel will have a similar level of fluorescence intensity at a certain blood glucose level. When using several fluorescent hydrogels of the present invention, their sizes may be equal to or different from each other.

The second of the present invention is a method for producing a fluorescent hydrogel.

The method for producing a fluorescent hydrogel of the present invention is not restricted, and is preferably, for example, a production method including (a1) a step of polymerizing an aqueous solution including a fluorescent monomer compound represented by the following chemical formula 5, a monomer represented by the following chemical formula 9 and a polymerizable monomer including a (meth)acrylamide residue; or a method for producing a fluorescent hydrogel including (a2) a step of polymerizing an aqueous solution including a fluorescent monomer compound represented by the following chemical formula 5, a monomer represented by the following chemical formula 10 and a polymerizable monomer including a (meth)acrylamide residue, and (b) a step of reacting a compound represented by the following chemical formula 11. Such production methods will now be described in detail. It should be noted, however, that the present invention is not restricted to these modes.

[Chem. 8]

[Chemical Formula 5]

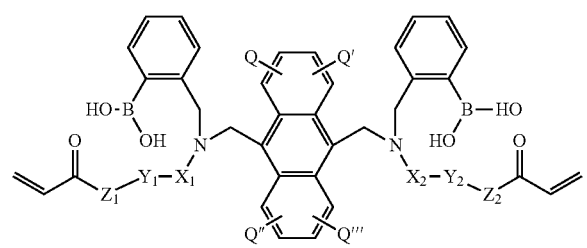

In the chemical formula 5, $X_1$, $X_2$, $Z_1$, $Z_2$, $Y_1$, $Y_2$, $Q$, $Q'$, $Q''$ and $Q'''$ have the same definitions as in the chemical formula 1.

[Chem. 9]

[Chemical Formula 9]

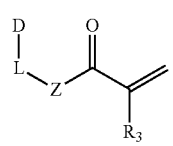

In the chemical formula 9, $R_3$ is a hydrogen atom or methyl, and D is a group represented by the following chemical formula 6,

[Chem. 10]

[Chemical Formula 6]

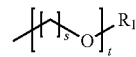

in the chemical formula 6, $R_1$ is a hydrogen atom, or straight or branched C1-10 alkyl, s is an integer from 2 to 5, and t is an integer from 1 to 200, Z, which may be the same or different, is —O— or —NR'—, in this case, R' is a hydrogen atom, or substituted or unsubstituted straight or branched C1-10 alkyl, L is a group selected from the group consisting of a single bond, —$U_5$—, —$U_5$—$NR_2$—, —$U_5$—O—, —$U_5$—S—, —$U_5$—SS—, —$U_5$—$NR_2$CO, —$U_5$—$CONR_2$—, —$U_5$—OCO—, —$U_5$—COO—, a group represented by the following chemical formula 7 and a group represented by the following chemical formula 8,

[Chem. 11]

[Chemical Formula 7]

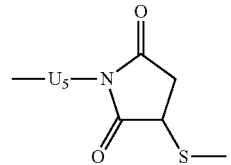

[Chem. 12]

[Chemical Formula 8]

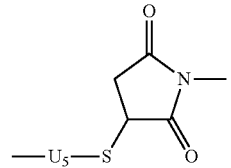

in this case, $U_5$ is substituted or unsubstituted straight or branched C1-10 alkylene, and $R_2$ is a hydrogen atom, or substituted or unsubstituted straight or branched C1-10 alkyl.

[Chem. 13]

[Chemical Formula 10]

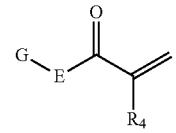

In the chemical formula 10, E is —O— or —NR'—, in this case, R' is a hydrogen atom, or substituted or unsubstituted C1-10 alkyl, G is substituted or unsubstituted straight or branched C1-10 alkyl which includes a reactive functional group at its end, and $R_4$ is a hydrogen atom or methyl.

[Step of Polymerizing an Aqueous Solution ((a1) or (a2))]

In this step, each monomer is turned into the form of an aqueous solution, and a polymerization reaction is carried out in the state of an aqueous solution. The difference between the step (a1) and the step (a2) is that monomers to be used are different. In the step (a1) which uses a monomer represented by the above chemical formula 9, a structure represented by the above chemical formula 6 (polyalkylene oxide structure) is introduced into a fluorescent hydrogel by this step to obtain the fluorescent hydrogel of the present invention. In the step (a2) which uses a monomer represented by the above chemical formula 10, a structure represented by the above chemical formula 6 (polyalkylene oxide structure) is introduced into a fluorescent hydrogel by carrying out this step and the step (b) of reacting a compound represented by the chemical formula 11, described below, to obtain the fluorescent hydrogel of the present invention.

The fluorescent monomer compound has a structure represented by the above chemical formula 5. Among this, a method for producing 9,10-bis[[N-(2-boronobenzyl)-N-[6-[(acryloylpolyoxyethylene)carbonylamino]hexyl]amino]methyl]-2-acetylanthracene (which is a compound wherein, in the above chemical formula 5, $X_1$ and $X_2$ are —$C_6H_{12}$—NHCO—, $Y_1$ and $Y_2$ are polyethylene glycol residues wherein n is 2 in the above chemical formula 3, $Z_1$ and $Z_2$ are —O—, Q is acetyl, Q', Q" and Q''' are hydrogen atoms: hereinafter simply referred to as "F-PEG-AAm"), which is a preferred compound as the fluorescent monomer compound, will be described by reference to the following reaction formula 1. It should be noted, however, that the present invention is not restricted thereto.

[Chem. 14]

[Reaction formula 1]

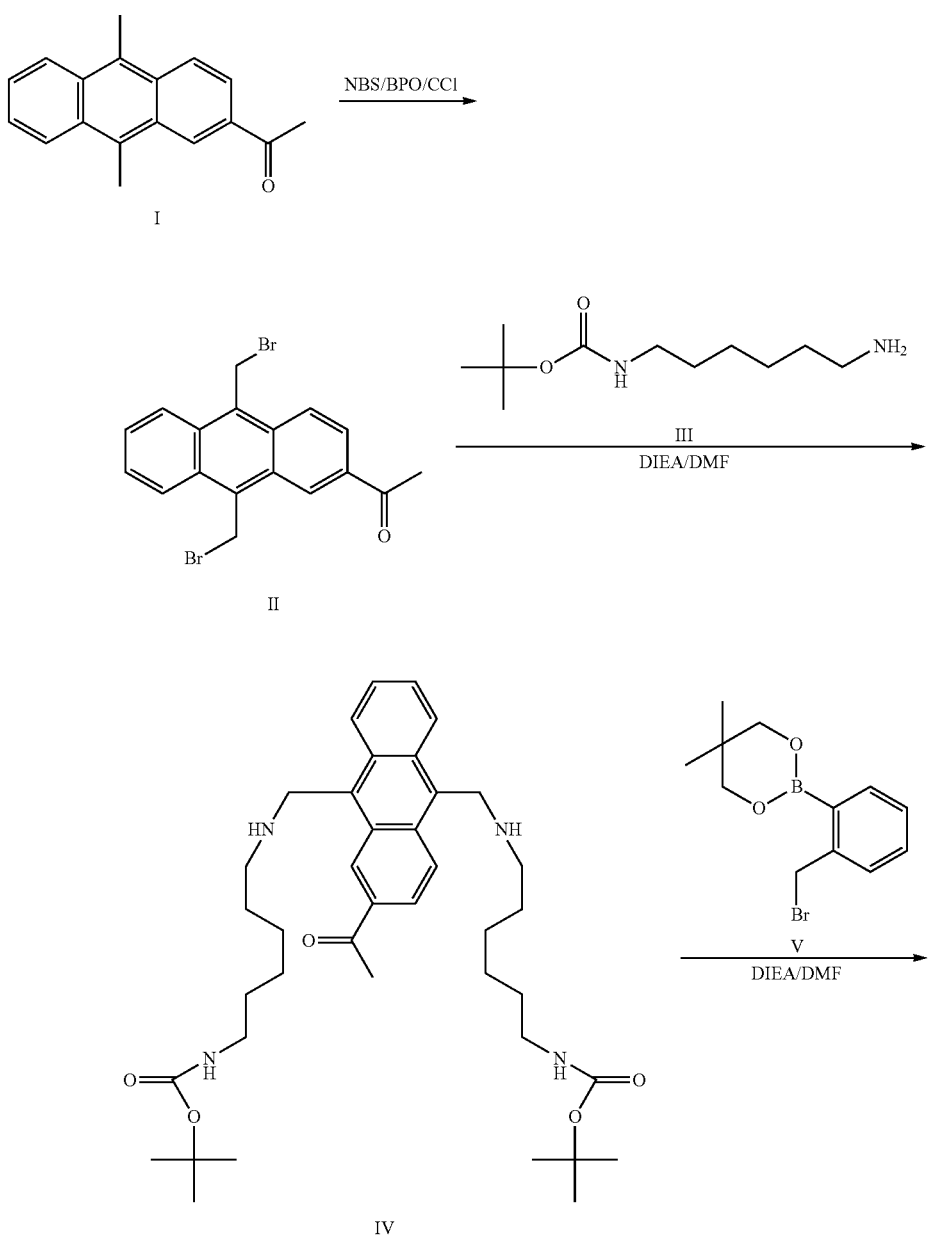

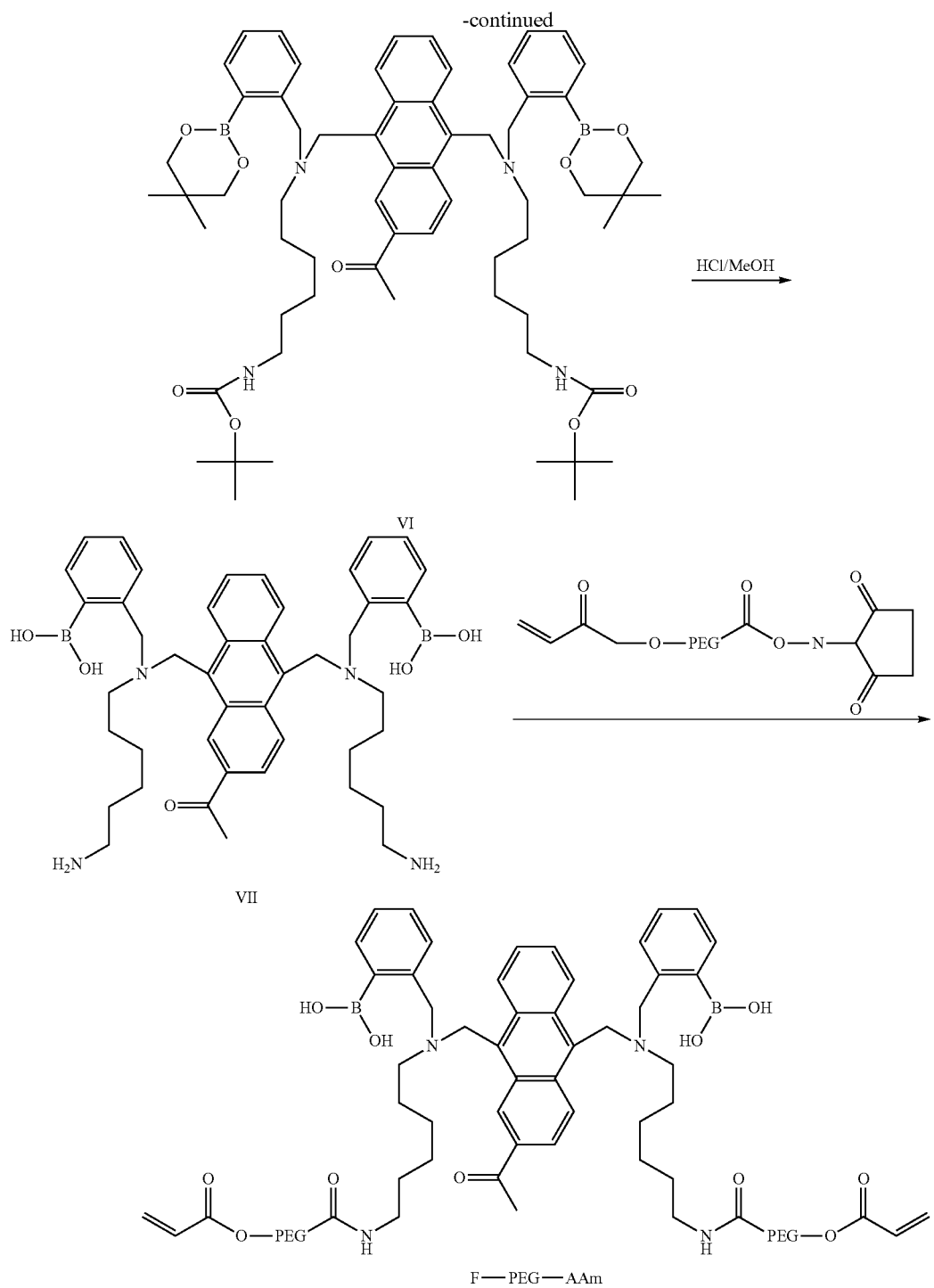

Using 2-acetyl-9,10-dimethylanthracene (I in the above reaction formula 1) as a raw material, this is reacted with N-bromosuccinimide (NBS) and benzoylperoxide (BPO) in a mixed solvent of carbon tetrachloride ($CCl_4$)/chloroform with heating to obtain 2-acetyl-9,10-bis(bromomethylene) anthracene (II in the above reaction formula 1). Then, upon reacting this with N-(t-butoxycarbonyl)-hexyldiamine (III in the above reaction formula 1) in the presence of a base such as diisopropylethylamine (DIEA) in a solvent such as N,N-dimethylformamide (DMF), bromomethylene group is turned into [(t-butoxycarbonylamino)hexylamino]methylene group (IV in the above reaction formula 1). To this, 2-(2-bromomethylphenyl)-1,3-dioxaborinane (V in the above reaction formula 1) is affected in the presence of a base such as DIEA in a solvent such as DMF to obtain 9,10-bis[[N-6'-(t-butoxycarbonylamino)hexyl-N-[2-(5,5-dimethylborinan-2-yl)benzyl]amino]methyl]-2-acetylanthracene (VI in the above reaction formula 1). To this, an acid such as hydrochloric acid is affected for deprotection to obtain 9,10-bis[[N-(6'-aminohexyl)-N-(2-boronobenzyl)amino]methyl]-2-acetylanthracene (VII in the above reaction formula 1). Then, upon reacting acryloyl-(polyethyleneglycol)-N-hydroxysuccinimide ester therewith in a basic buffer, F-PEG-AAm, the intended substance, can be obtained.

When using a compound having acyl other than acetyl in the anthracene skeleton as a raw material compound, a compound having acyl other than acetyl in the anthracene skeleton can be produced by properly selecting a solvent, additives, reaction temperature, reaction time, a separation method and the like.

As the polymerizable monomer including a (meth)acrylamide residue, a polymer to be obtained only has to have (meth)acryloyl group and amide in its structure, and (meth)acrylamide or a derivative thereof is preferred. Specific examples thereof include, for example, acrylamide, methacrylamide, N,N-dimethylacrylamide, N-isopropylacrylamide, N-tert-butylacrylamide, N-tris-hydroxymethylacrylamide, N-hydroxymethylacrylamide or N-(n-butoxymethyl) acrylamide, and the like. A condensate of (meth)acryloyl chloride such as N-acryloyl lysine or N-acryloyl hexamethylene diamine and an amino acid or a compound having an active amino group can be also used. Acrylamide or methacrylamide is more preferred.

A monomer represented by the above chemical formula 9, which monomer is used in the step (a1), is a monomer having a polyalkylene oxide structure in its molecule. More specific examples thereof include, for example, polyethylene glycol methyl ether acrylate, polypropylene glycol methyl ether acrylate, polyethylene glycol ethyl ether acrylate, polyethylene glycol ethyl acrylamide and the like.

A commercially available product may be used and a synthetic product may be used as a monomer represented by the above chemical formula 9. Examples of commercially available products include, for example, polyethylene glycol methyl ether acrylate (manufactured by Aldrich Co. LLC., Product number: 454990-250ML). Examples of synthesis methods for synthesizing the monomer include a method in which polyethyelne glycol and acryloyl chloride are reacted.

A monomer represented by the above chemical formula 10, which monomer is used in the step (a2), has substituted or unsubstituted straight or branched C1-10 alkyl having a reactive functional group at its end (G in the chemical formula 10), and the reactive functional group and a group represented by $J_2$ in the chemical formula 10 described below are reacted to introduce a polyalkylene oxide structure into a fluorescent hydrogel.

Specific examples of reactive functional groups contained in G in the chemical formula 10 include, for example, halogen, hydroxyl, aldehyde, N-hydroxysuccinimide, amino, carboxyl, thiol, maleimide, carboxylic acid ester, isothiocyanate, alkylsulfonyloxy and the like.

A group represented by G in the chemical formula 10 may be a group including a so-called spacer group on between the reactive functional group and a group represented by E in the chemical formula (10). The spacer group is preferably straight or branched C1-10 alkylene, aminoalkyl, oxyalkyl or the like, and more preferably straight or branched C1-5 alkylene. The spacer group may contain at least one bond selected from the group consisting of an amide bond, an imide bond, an ether bond, an ester bond, a thioether bond and a sulfonamide bond therein.

Examples of the straight or branched C1-10 alkylene are the same as above, and thus the explanation is omitted here. More specific examples of a compound represented by the chemical formula 10 include, for example, N-(2-aminoethyl) acrylamide, N-(3-aminopropyl)acrylamide, N-(2-aminoethyl) methacrylamide, N-(3-aminopropyl) methacrylamide and the like.

A commercially available product may be used and a synthetic product may be used as a monomer represented by the chemical formula 10. Examples of commercially available products include, for example, N-(3-aminopropyl)methacrylamide (manufactured by Polysciences, Inc., Product number: 21200-5). Examples of synthesis methods for synthesizing the monomer include a method in which alkyldiamine and acryloyl chloride are reacted.

In this step, a fluorescent monomer compound, a polymerizable monomer including a (meth)acrylamide residue and a polymerizable monomer including a monomer represented by the above chemical formula 9 or a monomer represented by the above chemical formula 10 are turned into the form of an aqueous solution.

The solvent of the above aqueous solution is not restricted, and distilled water, ion exchanged water, pure water, ultrapure water and the like can be used. An aqueous solution in which each of the above monomers is added to a phosphate buffer can be also used.

The concentration of a fluorescent monomer compound in an aqueous solution is preferably 1 to 30% by weight, and more preferably 2 to 10% by weight. The concentration of a polymerizable monomer including a (meth)acrylamide residue in an aqueous solution is preferably 5 to 50% by weight, and more preferably 10 to 20% by weight. The concentration of a monomer represented by the above chemical formula 9 or a monomer represented by the above chemical formula 10 in an aqueous solution is preferably 1 to 50% by weight, and more preferably 3 to 15% by weight.

Other components may be contained in the aqueous solution. Examples of such components include a polymerization initiator, a polymerization accelerator, a crosslinking agent, a cationic monomer which can be a cation in water, an anionic monomer which can be an anion in water or a nonionic monomer which does not have an ion, and the like. The details of the polymerization initiator, the polymerization accelerator and the crosslinking agent will be described below.

Examples of the cationic monomer which can be a cation in water can include, for example, dimethylaminoethyl(meth) acrylate, diethylaminoethyl(meth)acrylate or 4-vinylpyridine, and the like. These may be used individually, or two or more may be used in combination.

Examples of the anionic monomer which can be an anion in water can include, for example, (meth)acrylic acid, vinylpropionic acid or 4-vinylbenzene sulfonic acid, and the like. These can be used individually, or two or more can be used in combination.

Examples of the nonionic monomer which does not have an ion can include, for example, 2-hydroxyethyl(meth)acrylate, 3-methoxypropyl(meth)acrylate, 4-hydroxybutyl(meth) acrylate, 2-methoxyethyl acrylate or 1,4-cyclohexane dimethanol monoacrylate, and the like. These can be used individually, or two or more can be used in combination.

The compounding amount of these other components is preferably 0.1 to 10 mol % and more preferably 2 to 7 mol % relative to total amount of a fluorescent monomer compound, a polymerizable monomer including a (meth)acrylamide residue, and a monomer represented by the above chemical formula 9 or a monomer represented by the chemical formula 10.

The concentration of these other components in an aqueous solution is preferably 0.01 to 10% by weight, and more preferably 0.02 to 1.0% by weight. The details of the polymerization initiator, the polymerization accelerator and the crosslinking agent will be described below.

As described above, although the shape of the fluorescent hydrogel of the present invention is not restricted, it is preferred that, in this step, an aqueous solution be turned into a desired shape depending on the intended shape of a fluorescent hydrogel. For example, if aqueous solution droplets are produced in this step, fluorescent hydrogels in the shape of spheres are obtained. In addition, for example, if an aqueous solution column is produced in this step, a fluorescent hydrogel in the shape of a fiber is obtained. Methods for producing the above aqueous solution droplets and aqueous solution column will be now described. It should be noted, however, that the present invention is not restricted thereto.

Examples of the above methods for producing aqueous solution droplets from an aqueous solution include (1) a method in which an aqueous solution is added dropwise to an organic solvent; (2) a method in which an aqueous solution is added to an organic solvent which is stirred, and suspended and emulsified; and the like.

Examples of the organic solvents include, for example, cyclohexane, liquid paraffin, hexadecane, corn oil, mineral oil, silicone oil and the like. These can be used individually, or two or more can be used in combination. In terms of the stability of aqueous solution droplets, i.e. the inhibition of coalescence, silicone oil is more preferred.

The method for adding an aqueous solution to an organic solvent in the above (1) is not restricted, and the addition can be carried out, for example, using a microfluidic device having e.g. a two-dimensional T-junction (T intersection) and three-dimensional flow focusing; a microdispenser such as pipetman, a capillary syringe or an inkjet microdispenser; or a syringe, and the like. In particular, in terms of being able to easily control the particle diameter in the micro order, it is preferred that an axisymmetric flow-focusing device (hereinafter simply referred to as "AFFD"), a type of three-dimensional microfluidic devices, be used.

AFFD can be produced by stereo lithography (see Y. Morimoto et al., Biomed. Microdev., vol. 11 (2), pp. 369-377, 2009). There are the following two advantages by using AFFD.

(i) The size of aqueous solution droplets can be varied by controlling the flowing rate of an outer fluid, a continuous phase, to an inner fluid, a dispersed phase.

(ii) Because aqueous solution droplets do not come into contact with the surface of AFFD, aqueous solution droplets can be formed regardless of solution components (see S. Takeuchi et al., Adv. Mater., vol. 17, pp. 1067-1072, 2005; A. Luque et al., J. Microelectromech. Syst., vol. 16, pp. 1201-1208, 2007; and A. S. Utada et al., Science, vol. 308, pp. 537-541, 2005).

The suspension and emulsification in the above (2) can be carried out by adding an aqueous solution including a fluorescent monomer compound represented by the above chemical formula 1, a monomer represented by the above chemical formula 9 or a monomer represented by the above chemical formula 10 and a polymerizable monomer including a (meth)acrylamide residue to an organic solvent, which is stirred at an appropriate speed. The aqueous solution, which is added to the organic solvent, is divided in the form of droplets by shearing stress produced by stirring the organic solvent, and suspended in the organic solvent.

When the stability of aqueous solution droplets is low in the organic solvent, it is preferred that a surface active agent be used. Examples of surface active agents include, for example, sorbitan monoleate, sorbitan sesquioleate, polyoxyethylene(20)sorbitantrioleate, lecithin, trimethyl stearyl ammonium chloride, trimethyl cetyl ammonium chloride, trimethyl cetyl ammonium bromide, trimethyl n-tetradecyl ammonium chloride, alkyl benzene solfonic acid salts such as hard-type sodium dodecyl benzene sulfonate, soft-type sodium dodecyl benzene sulfonate and sodium 4-n-octyl benzene sulfonate, sulfuric acid ester salts such as sodium nonylphenol sulfate, further sodium dioctyl sulfosuccinate, sodium dodecyl sulfate and the like. These may be used individually, or two or more may be used in combination. When a surface active agent is added, it is added to either an aqueous solution in which a fluorescent monomer compound and the like are dissolved, or an organic solvent, or both.

In addition to the above method, fluorescent hydrogels in an almost spherical shape can be formed on the surface of a hydrophobic material such as glass, metal or plastics by adding dropwise micro-sized aqueous solution droplets with controlling their volumes to the surface from an inkjet device and so on, and further irradiating ultraviolet light or an electron beam.

The particle diameter of the aqueous solution droplets is preferably 10 nm to 2000 μm and more preferably 1 to 1000 μm. The particle diameter is particularly preferably 10 to 200 μm particularly for implantation using an injector, a cannula or a catheter and for using a microchannel. In this description, a value measured by a stereoscopic microscope is adopted as a particle diameter.

The shape and size of a fluorescent hydrogel to be ultimately obtained can be controlled depending on the shape and size of aqueous solution droplets to be obtained in this step. In the method for adding an aqueous solution to an organic solvent by AFFD, a microdispenser or the like, the size of aqueous solution droplets can be controlled by controlling the volumes of droplets. In the method in which an aqueous solution is added to an organic solvent which is stirred, and aqueous solution droplets are suspended, the size of aqueous solution droplets can be controlled by the stirring speed of the organic solvent, the viscosity of the aqueous solution and the organic solvent, and the like. In addition, only fluorescent hydrogels having a required particle diameter can be selected by putting the obtained fluorescent hydrogels through a sieve such as a filter.

Examples of the above method for producing an aqueous solution column from an aqueous solution include, for example, (1) a method using a tube; (2) a method using a minute channel; (3) a method using a coaxial microfluidic device; and the like.

The above method (1) using a tube is not restricted, and includes, for example, a method for producing an aqueous solution column by injecting an aqueous solution including a fluorescent monomer compound and a polymerizable monomer including a (meth)acrylamide residue into a tube.

FIG. 1 is a schematic diagram showing an aqueous solution column 12 filled in a tube 11. The aqueous solution column 12 is polymerized to become a fluorescent hydrogel fiber, and by taking this out from the tube 11, a fluorescent hydrogel fiber can be obtained.

Examples of materials for the tube include glass, metal such as aluminum and steel, plastics such as polyolefin, silicone, Teflon, and the like.

The injection of an aqueous solution into a tube is carried out using a syringe or the like, and an aqueous solution column can be obtained. After the injection of an aqueous solution into a tube, the both ends of the tube are plugged as needed. A fluorescent hydrogel can be obtained by polymerizing the aqueous solution column thus produced by various polymerization methods. In the method using a tube, fluorescent hydrogels in various shapes, in which the shapes of the section and length direction are varied, can be produced by varying the shape of the tube. The details of various polymerization methods will be described below.

The inside diameter and length of a tube can be properly set up depending on the size of an intended fluorescent hydrogel.

For example, the inside diameter of a tube is preferably 10 to 2000 μm, and the length of a tube is preferably 10 to 300 mm.

The polymerized fluorescent hydrogel in a tube can be taken out by carrying out operations such as squeezing the fluorescent hydrogel by pressure or the like, contracting the fluorescent hydrogel or cutting the tube and melting the tube. When taking a fluorescent hydrogel out by squeezing, the fluorescent hydrogel can be easily taken out by coating the inner wall of a tube with a surface active agent such as Pluronic (registered trademark), polyethylene glycol or a MPC polymer in advance.

Figure 2A:
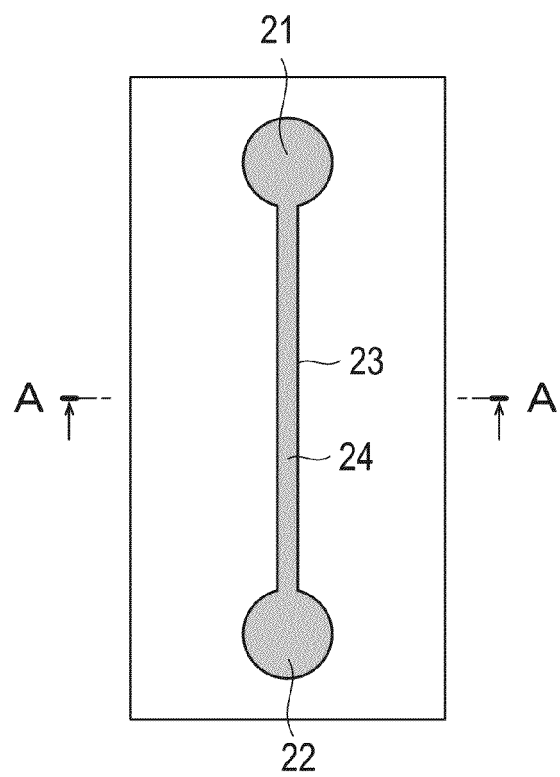
FIG. 2A is a schematic diagram showing an example of a minute channel producing an aqueous solution column.
Figure 2B:
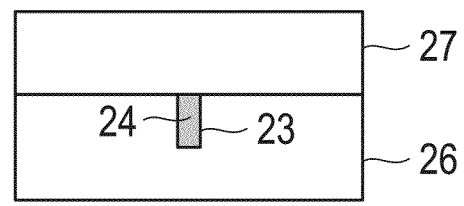
FIG. 2B is a schematic diagram showing a section on line A-A in FIG. 2A.

In the above method (2) using a microchannel (minute channel), one example of the microchannel (minute channel) to be used is shown in FIG. 2A. Upon injecting an aqueous solution including a fluorescent monomer compound and a polymerizable monomer including a (meth)acrylamide residue into the inlet 21 of the microchannel (minute channel), the aqueous solution flows into the outlet 22, and the aqueous solution column 24 can be produced in the microchannel (minute channel) 23. FIG. 2B is a schematic diagram showing a section on line A-A in FIG. 2A, and shows that an aqueous solution is injected into a space between the base plate 26 including the microchannel (minute channel) 23 and the base plate 27, which is put on the upper part of the base plate 26, to form the aqueous solution column 24. Examples of forming materials for the above microchannel (minute channel) include glass, polydimethylsiloxane, acrylic resin, poly(m-ethylmethacrylate) resin and the like.

A fluorescent hydrogel can be obtained by polymerizing the aqueous solution column thus produced by various polymerization methods. The details of various polymerization methods will be described below. In the method using a microchannel (minute channel), fluorescent hydrogels in various shapes, in which the shapes of the section and length direction are varied, can be produced by varying the shape of a channel.

The inside diameter and length of the microchannel (minute channel) can be properly set up depending on the size of an intended fluorescent hydrogel. For example, the inside diameter of a microchannel (minute channel) is preferably 10 to 2000 μm, and the length of a microchannel (minute channel) is preferably 10 to 3000 mm.

A fluorescent hydrogel, which is obtained by polymerization in a microchannel (minute channel), can be taken out by removing, from the base plate 26 including the microchannel (minute channel) 23, the base plate 27, which is put on the upper part thereof. When taking a fluorescent hydrogel out, the fluorescent hydrogel can be easily taken out by coating the inner wall of a microchannel (minute channel) with a surface active agent such as Pluronic (registered trademark), a polymer such as polytetrafluoroethylene, or octafluorocyclobutane ($C_4F_8$), and the like in advance.

Figure 3A:
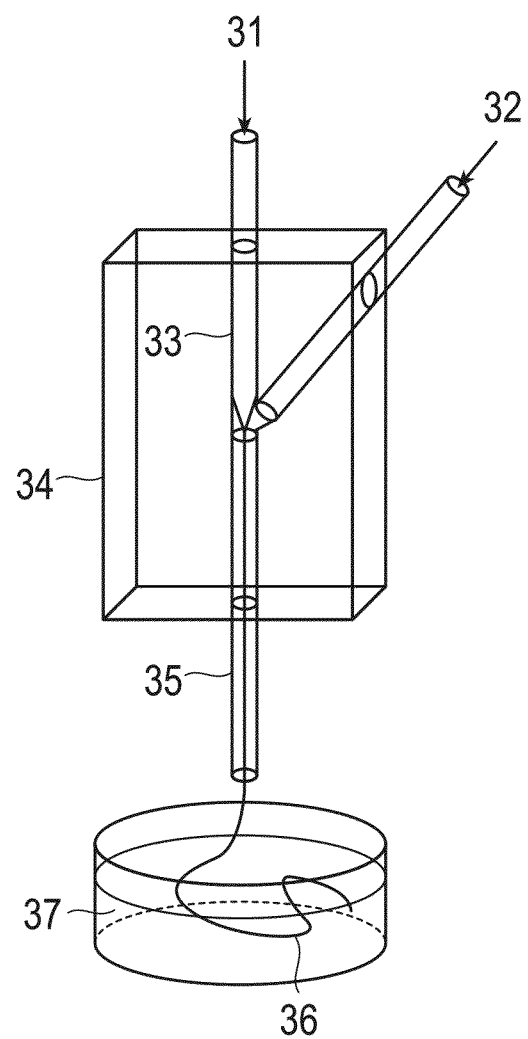
FIG. 3A is a schematic diagram showing the overall structure of a coaxial microfluidic device.
Figure 3B:
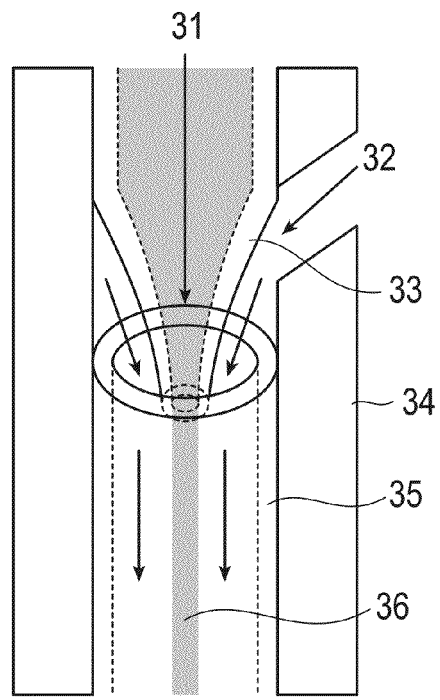
FIG. 3B is a schematic diagram showing the main part of FIG. 3A on a larger scale.

In the above method (3) using a coaxial microfluidic device, for example, the coaxial microfluidic device shown in FIG. 3A and FIG. 3B can be used. A microfluidic device, which can inject two fluids separately from a core part and a shell part in order that the fluids will be coaxial, is concretely illustrated in e.g. FIG. 1 of Lab Chip, 4, pp. 576-580, 2004. For example, an aqueous solution column in the core part can be produced in an organic solvent in the shell part by using an aqueous solution including a fluorescent monomer compound and a polymerizable monomer including a (meth)acrylamide residue as a fluid in the core part 31 and using the organic solvent which is not mixed with the aqueous solution as a fluid in the shell part 32. Examples of the organic solvents include, for example, cyclohexane, liquid paraffin, hexadecane, corn oil, mineral oil, silicone oil and the like. These can be used individually, or two or more can be used in combination. The fluorescent hydrogel of the present invention can be obtained by polymerizing the aqueous solution column by various polymerization methods. A solution having a composition to immediately polymerize an aqueous solution in the core part by contacting with the core part can be also used as a fluid in the shell part 32 in place of an organic solvent. The details of various polymerization methods will be described below.

The aqueous solution obtained in the above step (a1) or (a2) is then polymerized. The methods in which an aqueous solution is polymerized are not restricted, and include, for example, a chemical polymerization method using a radical polymerization initiator, a photopolymerization method using a photopolymerization initiator, or a radiation polymerization method by irradiating radiation, and the like.

The chemical polymerization method is carried out by adding a radical polymerization initiator and, if needed, a polymerization accelerator to an aqueous solution or an organic solvent, or both. The polymerization temperature is preferably 15 to 75° C., and more preferably 20 to 60° C. The polymerization time is preferably for 3 minutes to 20 hours, and more preferably 10 minutes to 8 hours. Examples of radical polymerization initiators can include, for example, a persulfate such as sodium persulfate, potassium persulfate or ammonium persulfate; hydrogen peroxide; an azo compound such as azobis-2-methylpropionamidine hydrochloride or azoisobutyronitrile; a peroxide such as benzoyl peroxide, lauroyl peroxide, cumen hydroperoxide or benzoyl oxide; and the like. These can be used individually, or two or more can be used in combination. In this case, for example, one or two or more of a reducing agent such as sodium hydrogen sulfite, sodium sulfite, Mohr's salt, sodium metabisulfite, formaldehyde sodium sulfoxylate or ascorbic acid; an amine compound such as ethylene diamine, sodium ethylene diamine tetraacetate, glycine or N,N,N',N'-tetramethyl ethylene diamine; and the like can be used as a polymerization accelerator.

The amount of a polymerization initiator is preferably 0.01 to 10% by weight as a concentration in an aqueous solution.

The photopolymerization method can be carried out, for example, by adding a photopolymerization initiator to an aqueous solution in advance, and irradiating ultraviolet light to the obtained aqueous solution in an organic solvent.

Examples of photopolymerization initiators to be used include, for example, acetophenone, 2,2-diethoxyacetophenone, p-dimethylaminoacetophenone, p-dimethylaminopropiophenone, p-dimethylaminopropiophenone, benzophenone, p,p'-dichlorobenzophenone, p,p'-bisdiethylamino benzophenone, Michler's ketone, benzyl, benzoin, benzoin methyl ether, benzoin isopropyl ether, benzoin-n-propyl ether, benzoin isobutyl ether, benzyl dimethyl ketal, 1-hydroxy-cyclohexylphenylketone, tetramethyl thiuram monosulfide, thioxanthone, 2-chlorothioxanthone, 2,4-dimethylthioxanthone, 2,2-dimethylpropioyl diphenylphosphine oxide, 2-methyl-2-ethylhexanoyl diphenylphosphine oxide, 2,6-dimethylbenzoyl diphenylphosphine oxide, 2,6-dimethoxybenzoyl diphenylphosphine oxide, 2,4,6-trimethylbenzoyl diphenylphosphine oxide, bis(2,6-dimethoxybenzoyl)-2,4,4-trimethylpentylphosphine oxide, 2,3,6-trimethylbenzoyl-diphenylphosphine oxide, bis(2,3,6-trimethylbenzoyl)-phenylphosphine oxide, 2,4,6-trimethoxybenzoyl-diphenylphosphine oxide, 2,4,6-trichlorobenzoyl diphenylphosphine oxide, 2,4,6-trimethylbenzoyl naphthylphosphonate, p-dimethylaminobenzoic acid, p-diethylamino benzoic acid, azobisisobutyronitrile, 1,1'-azobis(1-acetoxy-1-phenylethane), benzoin peroxide, di-tert-butyl peroxide and the like. These can be used individually, or two or more can be used in combination.

The wavelength of ultraviolet light is preferably 200 to 400 nm, and the amount of irradiation of ultraviolet light is preferably 100 to 2000 mJ/cm$^2$, and more preferably 500 to 1500 mJ/cm$^2$.

In the radiation polymerization method, radiation polymerization is carried out by irradiating radiation to an aqueous solution to be obtained. The radiation is preferably an electron beam, and the amount of irradiation is preferably 10 to 200 kGy, and more preferably 20 to 50 kGy.

When polymerization is carried out by an electron beam, polymerization can be carried out without using a polymerization initiator and a polymerization accelerator, in this case, the step of washing the polymerization initiator and accelerator is not required. The polymerization initiators and polymerization accelerators exemplified in the above chemical polymerization method can be also used.

The irradiation of electron beam can be carried out by an electron accelerator device. The device is classified into a low-energy type, a medium-energy type and a high-energy type depending on the magnitude of voltage for accelerating electrons. In polymerization of this step, a low-energy type electron accelerator device is preferred. Examples of low-energy type electron accelerator devices include, for example, a low-energy electron irradiation device manufactured by Hamamatsu Photonics K.K. This is a device in which thermoelectrons produced from a filament are accelerated at high voltage to increase energy, and an electron beam is taken out from a beryllium window foil to the atmosphere, and can irradiate electron beams at an acceleration voltage of 40 to 110 kV, which is relatively low.

After a fluorescent hydrogel is obtained in the above step, further the fluorescent hydrogel is preferably washed using a washing liquid. Examples of washing liquids include a phosphate buffer, pure water and the like.

When using an organic solvent in the above step (a1) or (a2), the dispersed phase of a fluorescent hydrogel is exchanged and washed, for example, by successively using a washing liquid A which can dissolve the organic solvent, and a washing liquid B which can dissolve the washing liquid A, and a fluorescent hydrogel can be ultimately obtained in an aqueous solution. Examples of washing liquids include, for example, alcohols, ethers, esters, ketones, hydrocarbons, halogen-containing hydrocarbons, buffer aqueous solutions, pure water and the like, preferably include methanol, ethanol, propanol, butanol, diethylether, ethyl acetate, acetone, heptane, hexane, cyclohexane, chloroform, methylene chloride, a phosphate buffer, pure water and the like, and more preferably include hexane, ethanol, a phosphate buffer, pure water and the like. These washing liquids can be used individually, or two or more can be used in combination. Among these, preferred is at least one selected from the group consisting of hexane, ethanol, a phosphate buffer and pure water.

[(b) Step of Reacting a Compound Represented by the Chemical Formula 11]

In this step, a reactive functional group (in the above chemical formula) in a hydrogel obtained when carrying out the above step (a2) and the $J_2$ moiety in a compound represented by the following chemical formula 11 are reacted to introduce a polyalkylene oxide structure into the fluorescent hydrogel.

[Chem. 15]

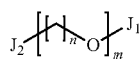

[Chemical Formula 11]

In the chemical formula 11, $J_1$ is a group including a hydrogen atom, substituted or unsubstituted straight or branched C1-10 alkyl, —$U_6$-halogen atom, —$U_6$—CHO, —$U_6$—SH, —$U_6$—NH$_2$, —$U_6$—NHR$_5$, —$U_6$—COOH, —$U_6$—COOR$_5$, —$U_6$—O-para-toluenesulfonyl, —$U_6$-isothiocyanate, —$U_6$—OCO—$U_6$-isothiocyanate, —$U_6$-maleimide, —$U_6$—NHCO—$U_6$-maleimide, —$U_6$—CONH—$U_6$-maleimide, —$U_6$—SO$_2$R$_5$, —$U_6$—OCOR$_5$, —$U_6$—(OR$_5$)$_2$, —$U_6$—COO-para-nitrophenyl, —$U_6$—OCO—$U_6$—COO—N-succinimide, or —$U_6$—COO—N-succinimide, and $J_2$ is a group including —O—$U_6$-halogen atom, —O—$U_6$—CHO, —O—$U_6$—SH, —O—$U_6$—NH$_2$, —O—$U_6$—NHR$_5$, —O—$U_6$—COOH, —O—$U_6$—COOR$_5$, —O—$U_6$—O-para-toluenesulfonyl, —O—$U_6$-isothiocyanate, —OCO—$U_6$-isothiocyanate, —O—$U_6$-maleimide, —O—$U_6$—NHCO—$U_6$-maleimide, —O—$U_6$—CONH—$U_6$-maleimide, —O—$U_6$—OSO$_2$R$_5$, —O—$U_6$—OCOR$_5$, —O—$U_6$—(OR$_5$)$_2$, —O—$U_6$—COO-para-nitrophenyl, —OCO—$U_6$—COO—N-succinimide, or —O—$U_6$—COO—N-succinimide, in this case, $U_6$ is substituted or unsubstituted straight or branched C1-10 alkylene, $R_5$ is a hydrogen atom, or substituted or unsubstituted straight or branched C1-10 alkyl, n is 2 to 5, and m is 1 to 200.

A commercially available product may be used and a synthetic product may be used as a compound represented by the chemical formula 11. Examples of commercially available products include, for example, polyethylene glycol-pentyl-carbonyloxy-N-succinimide (manufactured by NOF CORPORATION, Product number: SUNBRIGHT ME-050HS). Examples of synthesis methods for synthesizing the compound include a method in which polyethylene glycol and alkyl dicarboxylic acid are reacted.

As the combination of $J_1$ or $J_2$ and a reactive functional group contained in G, various reactions are adopted depending on combination of functional groups which produce a bond each other, and the combination is not restricted. For example, in the case of the combination in which one side is hydroxyl, amino or thiol and the other side is halogen, oxysulfonylalkyl, activated ester or COO—N-succinimide, the reaction is a nucleophilic reaction. In the case of the combination in which one side is hydroxyl, amino or thiol, and the other side is carboxylic acid, the reaction is a dehydration-condensation reaction.

A crosslinked structure can be also formed by using a compound including reactive functional groups on both $J_1$ and $J_2$.

In the reaction of this step, reaction conditions such as a solvent to be used, a reaction catalyst, reaction atmosphere, reaction temperature and reaction time, and the like can be varied depending on a reaction to be adopted. To give an example, reaction time is preferably 0.5 to 20 hours and reaction temperature is preferably 0 to 100° C. for a nucleophilic reaction. In addition, there can properly exist reaction aids such as a base, an acid, a catalyst, a dehydration-condensation agent, a solubilizing agent and an activator.

The concentration of a compound represented by the chemical formula 11 in an aqueous solution is preferably 0.1 to 20% by weight, and more preferably 1 to 5% by weight.

The fluorescent hydrogel obtained by the production method of the present invention as described above has a structure represented by the above chemical formula 1. The detail structure is the same as the contents described above, and thus the explanation is omitted here.

A fluorescent hydrogel having a structure represented by the above chemical formula 1 can be also produced by a production method other than the production method including the above step (a1) or the production method including the above step (a2) and step (b).

For example, a fluorescent hydrogel having a structure represented by the above chemical formula 1 can be also produced by a production method in which an aqueous solution including a polymer obtained by polymerizing a polymerizable monomer having a (meth)acrylamide residue in advance, a fluorescent monomer compound represented by the above chemical formula 5, a monomer represented by the above chemical formula 9 or a monomer represented by the above chemical formula 10, a polymerization initiator and, if needed, a polymerization accelerator is added to an organic solvent to produce a solution, and the obtained solution is polymerized by the above polymerization methods.

The fluorescent hydrogel of the present invention may have a three-dimensional crosslinked structure. The introducing methods of a three-dimensional crosslinked structure are not restricted, and include, for example, a method in which a crosslinking agent is applied to the fluorescent hydrogel of the present invention to form an intermolecular crosslinking on at least one part between a fluorescent monomer compound represented by the above chemical formula 5, a polymerizable monomer including a (meth)acrylamide residue and a monomer represented by the above chemical formula 9 or a monomer represented by the above chemical formula 10. By forming a three-dimensional crosslinking on a poly(meth)acrylamide chain, saccharides can be easily detected without elution of a fluorescent monomer compound even in an aqueous solution. Although a fluorescent monomer compound used in the present invention has a hydrophobic region which emits fluorescence by binding to saccharides, the hydrophobic region is bound to a poly(meth)acrylamide chain via divalent organic residues represented by $Y_1$ and $Y_2$ in the above chemical formula 1, and thus a degree of freedom of the hydrophobic region is secured as the hydrophobic region binds to saccharides even in an aqueous solution. Therefore, even when a three-dimensional crosslinked structure is formed, the detection sensitivity of saccharides is hardly reduced.

The crosslinking agents widely contain those which can introduce a three-dimensional crosslinked structure into a fluorescent sensor compound by a polymerizable double bond. Specific examples thereof include, for example, divinyl compounds such as N,N'-methylene bis(meth)acrylamide, N,N'-(1,2-dihydroxyethylene)-bis(meth)acrylamide, diethyleneglycol di(meth)acrylate, (poly)ethylene glycol di(meth)acrylate, triethylene glycol di(meth)acrylate, propylene glycol di(meth)acrylate, trimethylolpropane di(meth)acrylate, trimethylolpropane tri(meth)acrylate, pentaerythritol di(meth)acrylate, pentaerythritol tri(meth)acrylate, pentaerythritol tetra(meth)acrylate, (poly)propylene glycol di(meth)acrylate, glycerin tri(meth)acrylate, glycerin acrylate methacrylate, ethylene oxide modified trimethylol propane tri(meth)acrylate, pentaerythritol tetra(meth)acrylate and dipentaerythritol hexa(meth)acrylate; triallyl cyanurate, triallyl isocyanurate, triallyl phosphate, triallylamine, poly(meth)allyloxyalkane, (poly)ethylene glycol diglycidyl ether, glycerol diglycidyl ether, ethylene glycol, polyethylene glycol, propylene glycol, glycerin, pentaerythritol, ethylenediamine, polyethylene imine, glycidyl(meth)acrylate, triallyl isocyanurate, trimethylol propane di(meth)allyl ether, tetraallyloxyethane or glycerol propoxytriacrylate, and the like. These crosslinking agents can be used individually, or two or more can be used in combination.

The amount of a crosslinking agent is preferably 0.01 to 10% by weight as a concentration in an aqueous solution column.

A fluorescent hydrogel obtained in the present invention can be used as a component of an implantable sensor for measuring saccharides. The fluorescent hydrogel of the present invention can be implanted in a living body with minimal invasiveness. Implantation methods include a burying method using an injector, a cannula, an indwelling needle or a catheter, or a burying method by exfoliating a part of the surface layer of the skin, and the like. Further, when an implanted fluorescent hydrogel is in the shape of fibers, the whole fluorescent hydrogel, which is implanted in a living body, can be removed by pinching its end and pulling out. That is, the present invention also provides a method for using such fluorescent hydrogel.

Because the fluorescent hydrogel of the present invention has a highly biocompatible poly(meth)acrylamide structure, it has less influence on a living body by long term implantation in the living body.

The fluorescent hydrogel of the present invention does not undergo chemical degradation such as hydrolysis and enzymatic degradation in a living body, and thus it is believed to have the high stability of long term implantation. Tissues to be implanted are preferably the intradermal and subcutaneous tissues, and more preferably the dermis layer, in which an exchange of blood and body fluid is active and which is at a shallow depth from the surface skin, to achieve high sensitivity and short time lag. The place of implantation is not restricted as long as it is a place where optical measurements can be carried out from the surface of the skin, and includes, for example, arms, legs, abdomen, ears and the like. When a fluorescent hydrogel is, for example, in the shape of fibers, it can be fixed in a living body by sewing or winding in subcutaneous tissues and tissues in a body, and can be implanted regardless of the size and shape of regions and organs. For example, the fluorescent hydrogel can be fixed by sewing in subcutaneous tissues, a renal capsule, a pancreas capsule and the like and winding around a blood vessel and the like.

The fluorescent hydrogel of the present invention can be used as a component of an implantable sensor for measuring saccharides, which sensor has a means in which the fluorescent hydrogel of the present invention is implanted in a body, and excitation light is irradiated from the sensor, which is outside the body or implanted in the same region, to measure fluorescence emitted from the above fluorescent hydrogel.

In addition, the fluorescent hydrogel of the present invention can be used as a component of a sensor for measuring saccharides, which sensor has a means in which body fluid is circulated between a hollow needle, which is inserted into a body, and an external fluorescence detector system, which is connected to the hollow needle, and the fluorescent hydrogel is put on a part of the circulation path to measure fluorescence emitted from the fluorescent hydrogel.

The above circulation path is preferably one which has the properties of permeating saccharides, which are objects to be measured, but not permeating high molecules such as cells and proteins among body components. The body fluid passes through the circulation path on which a fluorescent hydrogel is put, and saccharides in the body fluid come into contact with the fluorescent hydrogel. The values, which reflect glucose concentrations in a living body, can be obtained by continuously measuring the fluorescence of the fluorescent hydrogel, which comes into contact with saccharides in the body fluid, using a fluorescence detector system.

The fluorescence detector system preferably includes at least one light source and at least one photodetector. It is preferred that the light source and the photodetector be arranged in order that excitation light emitted from the light source will be admitted thereto as little as possible and fluorescence emitted from a fluorescent hydrogel will be efficiently detected.

The measurement of fluorescent signals can be carried out by arranging a light source such as a lamp, a LED or a laser, which is suited to the fluorescent characteristics of a fluorescent hydrogel, and a light detector, and, if needed, a light, a lens, a mirror, a prism, an optical filter and the like in an appropriate position around sensor components.

Saccharides which can be detected using the fluorescent hydrogel of the present invention are not restricted, and include, for example, monosaccharides such as glucose, galactose and fructose and polysaccharides such as maltose, sucrose and lactose. Among these, glucose is more preferred.

The troublesomeness or time lag of blood glucose level when diabetics control their blood glucose level by themselves can be reduced by using the above-described sensor for measuring saccharides. Further, people other than people with diabetes can easily carry out blood glucose level measurements for health care by using the above-described sensor for measuring saccharides.

EXAMPLES

The present invention will now be described in more detail by way of examples thereof. It should be noted, however, that the examples do not restrict the present invention.

Example 1

Synthesis of 9,10-bis[[N-2-boronobenzyl)-N-[6-[(acryloylpolyoxyethylene)carbonylamino]hexyl]amino]methyl]-2-acetylanthracene (A) Synthesis of 9,10-bis(bromomethyl)-2-acetylanthracene (II in the above reaction formula 1)

To a mixture of 6 mL of chloroform and 20 mL of carbon tetrachloride, 600 mg of 9,10-dimethyl-2-acetylanthracene (I in the above reaction formula 1), 800 mg of N-bromosuccinimide and 5 mg of benzoyl peroxide were added, and the obtained mixture was fluxed at 80° C. for 2 hours. The solvent was removed, and the residue was then extracted with methanol to obtain 780 mg of the intended substance.

(B) Synthesis of 9,10-bis[6'-(t-butoxycarbonylamino)hexylaminomethyl]-2-acetylanthracene (IV in the above reaction formula 1)

In 10 mL of N,N-dimethylformamide (DMF), 500 mg of the product obtained in the above (A), 1.125 g of N—BOC-hexyldiamine (III in the above reaction formula 1) and 1.25 mL of diisopropylethylamine were dissolved, and the obtained mixture was stirred at 45° C. for 1 hour to carry out a reaction. The reaction mixture was diluted with 60 mL of chloroform, and washed three times with 100 mL of water and once with 100 mL of saturated sodium chloride water, and the organic phase was dried with anhydrous sodium sulfate. The drying agent was filtered, and the filtrate was then concentrated and purified by silica gel column chromatography using a chloroform/methanol (volume ratio, 95/5) mixed solvent as an eluent to obtain 367 mg of the intended substance.

(C) Synthesis of 9,10-bis[[N-6'-(t-butoxycarbonylamino)hexyl-N-[2-(5,5-dimethylborinan-2-yl)benzyl]amino]methyl]-2-acetylanthracene (VI in the above reaction formula 1)

In 3 mL of dimethylformamide, 200 mg of the product obtained in the above (B), 700 mg of 2-(2-bromomethylphenyl)-1,3-dioxaborinane (V in the above reaction formula 1) and 0.35 mL of N, N-diisopropylethylamine were dissolved, and the obtained mixture was stirred at room temperature (25° C.) for 16 hours. The solvent was removed, followed by purification by silica gel column chromatography using methanol/chloroform as an eluent to obtain 194 mg of the intended substance.

(D) Synthesis of 9,10-bis[[N-(6'-aminohexyl)-N-(2-boronobenzyl)amino]methyl]-2-acetylanthracene (VII in the above reaction formula 1)

In 2 mL of methanol, 100 mg of the product obtained in the above (C) was dissolved, and 2 ml of 4 N hydrochloric acid was added thereto. The obtained mixture was stirred at room temperature (25° C.) for 10 hours. After evaporation to dryness, inorganic salts were removed by gel filtration to obtain 95 mg of the intended substance.

(E) Synthesis of F-PEG-AAm

In 0.5 mL of DMF, 160 mg of the product obtained in the above (D) was dissolved, and the obtained mixture was added to 1.22 g of acryloyl-(polyethyleneglycol)-N-hydroxysuccinimide ester (the molecular weight of the polyethylene glycol residue moiety is 3,400) in 10 mL of a 100 mM phosphate buffer (pH=8.0) solution. The obtained mixture was stirred at room temperature (25° C.) for 20 hours. The reaction mixture was subjected to gel filtration, and fluorescent high molecular fractions were collected, followed by freeze-drying to obtain 1.2 g of F-PEG-AAm, the intended substance. The $^1$H-NMR data measured by using deuterated chloroform are as in the following Table 1, and a hydrogen signal overlapping a peak derived from the polyethylene glycol (PEG) residue was not detected.

TABLE 1

$^1$H-NMR (CDCl$_3$): δ 1.30-1.65 (m, C—CH$_2$—C), 2.90 (s, Ac), 2.78 (m, —C(—C)N—CH$_2$—C), 3.25 (m, CH$_2$—NH—COO), 3.50-3.80 (s, PEG), 5.80 (d, COCH=C), 6.17 (m, C=CH$_2$), 7.20-8.20 (m, aromatic)

Example 2

Production of a Fluorescent Hydrogel

Here, a fluorescent hydrogel was produced by the above method (a1). In order that the concentration of acrylamide would be 15% by weight, the concentration of N,N'-methylene bisacrylamide would be 0.3% by weight, and the concentration of polyethylene glycol methyl ether acrylate (manufactured by Aldrich Co. LLC., Product number 454990-250ML, average molecular weight: 480, hereinafter simply referred to as "PEG acrylate") would be 0, 1, 5 and 10% by weight, the substances were each added to a 60 mM phosphate buffer (pH 7.4), dissolved and mixed to prepare 4 types of aqueous solution in total. PEG acrylate used here is a compound wherein s is 2, t is 8 to 9 as a mixture, R$_1$ is methyl, R$_3$ is a hydrogen atom, Z is —O—, and L is a single bond in the above chemical formula 9. The four types of aqueous solution were each subjected to nitrogen bubbling at room temperature (25° C.).

In order that the concentration of F-PEG-AAm synthesized in Example 1 would be 5% by weight, the concentration of sodium persulfate would be 1.8% by weight, and the concentration of N,N,N',N'-tetramethyl ethylene diamine would be 0.2% by weight, the substances were each added to the obtained aqueous solution.

The above aqueous solution was sucked up into a polyolefin tube, wherein the tube had been coated with Pluronic (registered trademark) to easily remove a fluorescent hydrogel to be produced, and the tube was placed on a hot plate at 37° C. to initiate polymerization. The polyolefin tube with an inner diameter of 700 μm and a length of 70 mm was used.

Figure 4:
FIG. 4 is a photograph of the fluorescent hydrogel obtained in Example 2.

After 5 hours, a fluorescent hydrogel obtained by polymerization was taken out from the polyolefin tube by applying air pressure, and immersed in a large amount of pure water for washing for over 24 hours. A photograph of the obtained fluorescent hydrogel with a diameter of 700 μm is shown in FIG. 4.

Example 3

Confirmation of Glucose Responsiveness

The fluorescent hydrogel with a diameter of 700 μm obtained in Example 2 (PEG acrylate 5% by weight) was immersed in a 60 mM phosphate buffer, which had been prepared in order that the concentration of glucose would be in a range from 0 to 1000 mg/dL, and the fluorescence intensity of the fluorescent hydrogel at each glucose concentration was observed by a fluorescence stereoscopic microscope. The results are shown in FIG. 5.

Figure 5:
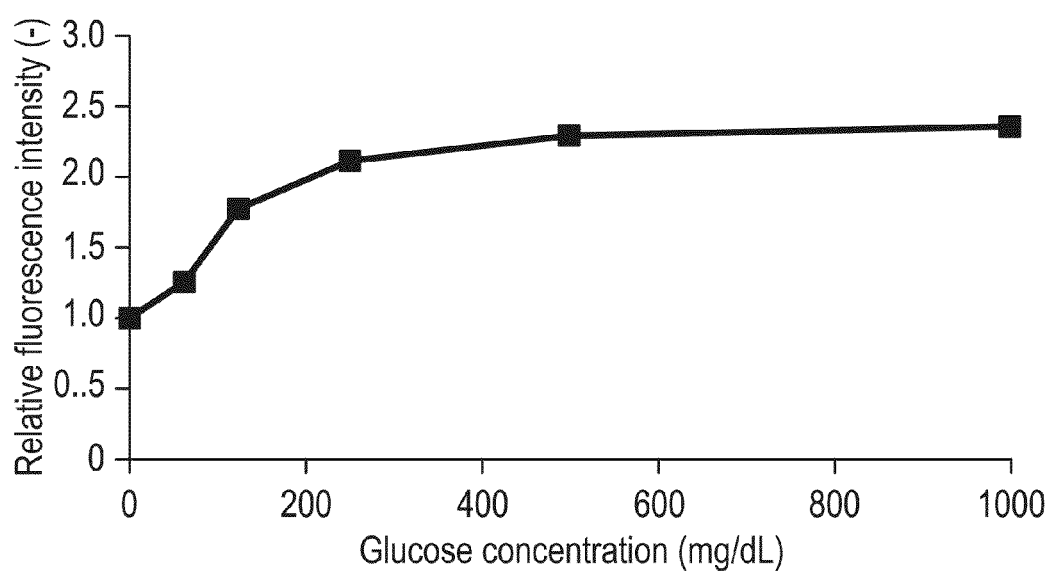
FIG. 5 is a graph showing the relationship between glucose concentrations and the fluorescence intensity of a fluorescent hydrogel.

As shown in FIG. 5, the fluorescent hydrogel has glucose responsiveness, and it could be confirmed that glucose concentrations could be measured by using the fluorescent hydrogel of the present invention.

Example 4

Analysis by FT-IR

Figure 6:
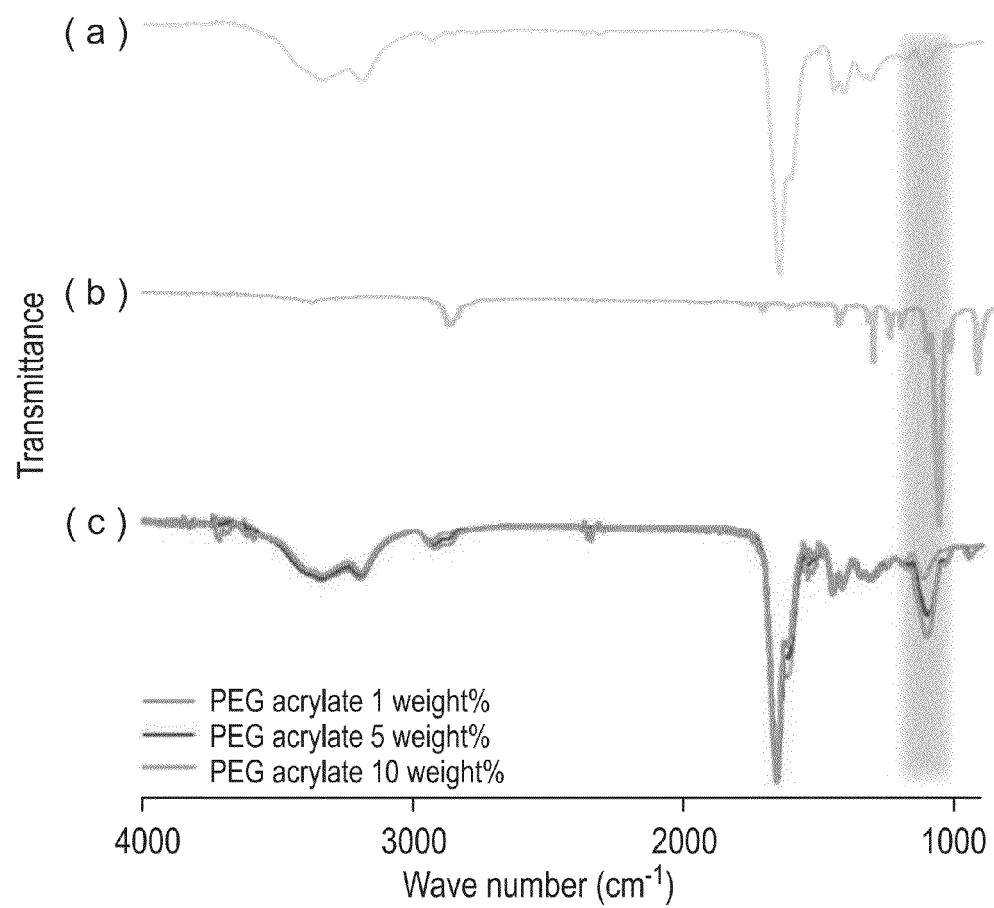
FIG. 6($a$) is the FT-IR spectrum of only AAm gel produced without using F-PEG-AAm and polyethylene glycol methyl ether acrylate in the method of Example 2, FIG. 6($b$) is the FT-IR spectrum of only polyethylene glycol methyl ether acrylate, and FIG. 6($c$) is the FT-IR spectrum of a hydrogel produced without using F-PEG-AAm in the method of Example 2.

To confirm the introduction of a PEG structure into a fluorescent hydrogel, the FT-IR measurement of a hydrogel produced without using F-PEG-AAm in the method of Example 2 was carried out (FIG. 6(c)). The FT-IR measurement was carried out by an ATR method after freeze-drying of the produced hydrogel. As controls, the FT-IR spectrum of only AAm gel produced without using F-PEG-AAm and PEG acrylate in the method of Example 2 (FIG. 6(a)) and the FT-IR spectrum of only PEG acrylate (FIG. 6(b)) were also measured.

As shown in FIG. 6(c), a peak around 1100 $cm^{-1}$ derived from asymmetric stretching vibration of C—O in PEG could be confirmed in the hydrogel produced using PEG acrylate. On the contrary, the peak was not confirmed in AAm gel produced without using PEG. These results confirmed that a PEG structure could be introduced into a hydrogel by the polymerization method.

Example 5

Evaluation of the Ability to Inhibit Protein Adsorption

To evaluate the ability to inhibit protein adsorption of a fluorescent hydrogel, four types of fluorescent hydrogel (PEG acrylate 0, 1, 5 and 10% by weight) produced in Example 4 were immersed in a 1 mg/mL bovine serum albumin solution. After immersion at room temperature (25° C.) for 48 hours, the hydrogels were immersed in a 500 mM sodium chloride solution to elute bovine serum albumin adsorbed to the fluorescent hydrogels. The BCA assay was carried out on the eluate to determine the amount of bovine serum albumin adsorbed to the gel. The results are shown in FIG. 7.

Figure 7:
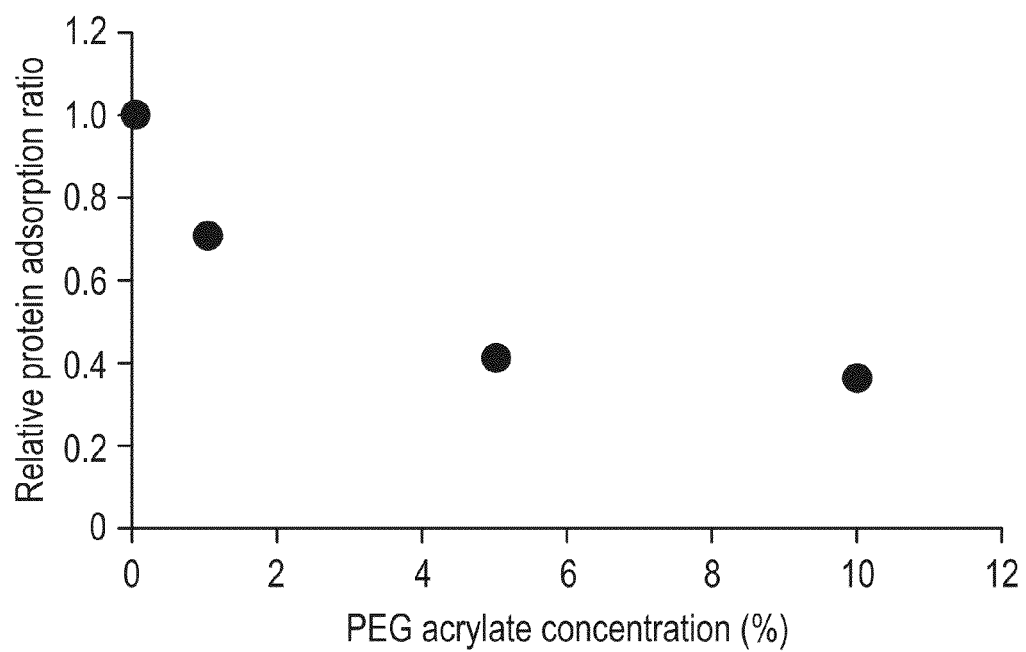
FIG. 7 is a graph showing the relationship between the concentration of polyethylene glycol methyl ether acrylate and the amount of bovine serum albumin adsorbed to the gel.

As shown in FIG. 7, it could be confirmed that as the concentration of PEG acrylate increased, the concentration of adsorbed bovine serum albumin decreased. It is believed that adsorption of bovine serum albumin to the gel was inhibited by the steric repulsion effect of PEG, and it could be confirmed that a PEG structure was useful for the inhibition of protein adsorption.

Example 6

Confirmation of Glucose Responsiveness in a Living Body

The fluorescent hydrogel with a diameter of 700 μm obtained in Example 2 (PEG acrylate 5% by weight) was cut into a length of about 25 mm, and the hydrogel was implanted in a mouse ear. A photograph at this time is shown in FIG. 8(a). A glucose solution and an insulin solution were administered via the jugular vein of the mouse, and changes in the fluorescence intensity of the fluorescent hydrogel in the living body when the blood glucose level of the mouse had been changed were observed. The results are shown in FIG. 8(b).

As shown in FIG. 8(b), it could be confirmed that the fluorescence intensity of the fluorescent hydrogel increased and decreased according to an increase and a decrease in blood glucose level.

Thus, it could be confirmed that the fluorescent hydrogel of the present invention could be used as an implantable sensor for measuring saccharides.

Example 7

Confirmation of Glucose Responsiveness in a Living Body after 72 Days from Implantation The same glucose tolerance test as in Example 6 was carried out after 72 days from implantation of a fluorescent hydrogel (PEG acrylate 5% by weight) in the same manner as in Example 6. A photograph of a mouse after 72 days from implantation of the fluorescent hydrogel is shown in FIG. 9(a), and changes in blood glucose level and changes in the fluorescence intensity of the fluorescent hydrogel, which has been implanted, in the glucose tolerance test are shown in FIG. 9(b).

As shown in FIG. 9(b), it could be confirmed that the fluorescence intensity of the fluorescent hydrogel increased and decreased in response to blood glucose level in the body even after a lapse of 72 days from implantation. Thus, it could be confirmed that the fluorescent hydrogel of the present invention could be used as a long-term (over 72 days) implantable sensor for measuring saccharides.

Example 8

Confirmation of Glucose Responsiveness in a Living Body after 140 Days from Implantation The same glucose tolerance test as in Examples 6 and 7 was carried out after 140 days from implantation of a fluorescent hydrogel (PEG acrylate 5% by weight) in the same manner as in Examples 6 and 7. A photograph of a mouse after 140 days from implantation of the fluorescent hydrogel is shown in FIG. 10(*a*), and changes in blood glucose level and changes in the fluorescence intensity of the fluorescent hydrogel, which has been implanted, in the glucose tolerance test are shown in FIG. 10(*b*).

As shown in FIG. 10(*b*), it could be confirmed that the fluorescence intensity of the fluorescent hydrogel increased and decreased in response to blood glucose level in the body even after a lapse of 140 days from implantation. Thus, it could be confirmed that the fluorescent hydrogel of the present invention could be used as a long-term (over 140 days) implantable sensor for measuring saccharides.

The present application is based on Japanese Patent Application No. 2010-222363, filed Sep. 30, 2010, and the disclosed contents are incorporated herein by reference in its entirety.

REFERENCE SIGNS LIST

11 Tube,
12, 24 Aqueous solution column,
21 Inlet of microchannel (minute channel),
22 Outlet of microchannel (minute channel),
23 Microchannel (minute channel),
26, 27 Base plate,
31 Fluid in the core part,
32 Fluid in the shell part,
33 Glass tube for injection,
34 Polydimethyl siloxane holder,
35 Glass tube for focusing,
36 Fluorescent hydrogel,
37 DI water.

The invention claimed is:

1. A fluorescent hydrogel, which has a structure represented by the following chemical formula 1:

[Chem. 1]

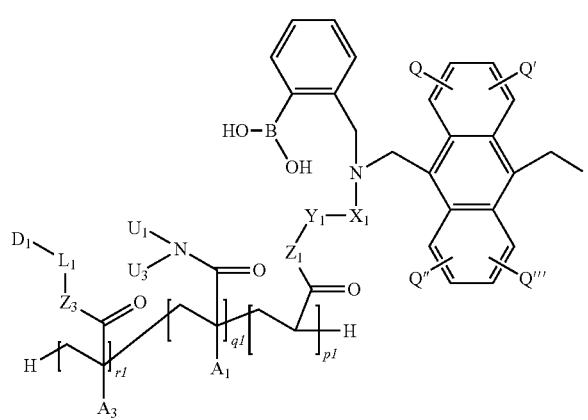

[Chemical Formula 1]

-continued

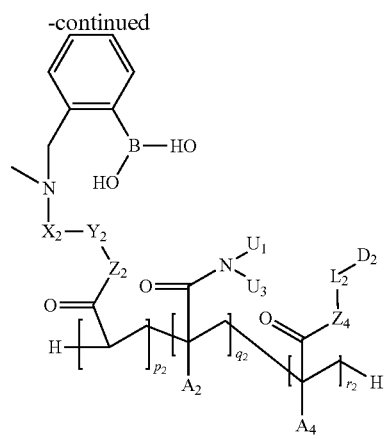

in the chemical formula 1, $X_1$ and $X_2$, which are optionally the same or different, are C1-30 alkylene which optionally comprises at least one substituent selected from the group consisting of —COO—, —OCO—, —CH$_2$NR—, —NR—, —NRCO—, —CONR—, —SO$_2$NR—, —NRSO$_2$—, —O—, —S—, —SS—, —NRCOO—, —OCONR— and —CO—, in this case, R is a hydrogen atom, or substituted or unsubstituted straight or branched C1-10 alkyl, $Z_2$, $Z_3$ and $Z_4$, which are optionally the same or different, are —O— or —NR'—, in this case, R' is a hydrogen atom, or substituted or unsubstituted straight or branched C1-10 alkyl, Q, Q', Q" and Q''', which are optionally the same or different, are hydrogen atoms, hydroxy, substituted or unsubstituted straight or branched C1-10 alkyl, C2-11 acyl, substituted or unsubstituted straight or branched C1-10 alkoxy, halogen atom-containing groups, carboxyl, carboxylic acid ester, carboxylic acid amide, cyano, nitro, amino or C1-10 alkylamino, and at least one of Q and Q', and Q" and Q''' optionally join together to form an aromatic ring or a heterocycle, $Y_1$ and $Y_2$, which are optionally the same or different, are divalent organic residues which are optionally substituted, or single bonds, in this case, at least one of $Y_1$ and $Y_2$ optionally contains a structure represented by the following chemical formula 3 or the following chemical formula 4,

[Chem. 2]

[Chemical Formula 3]

[Chem. 3]

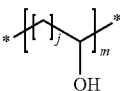

[Chemical Formula 4]

in the chemical formula 3 and the chemical formula 4, n is 2 to 5, j is 1 to 5, m is 1 to 200, and * represents a binding point, $A_1$, $A_2$, $A_3$ and $A_4$, which are optionally the same or different, are hydrogen atoms or methyl, $U_1$, $U_2$, $U_3$ and $U_4$, which are optionally the same or different, are hydrogen atoms, or substituted or unsubstituted straight or branched C1-10 alkyl, $D_1$ and $D_2$, which are optionally the same or different, are groups represented by the following chemical formula 6,

[Chem. 4]

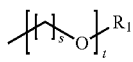
[Chemical Formula 6]

in the chemical formula 6, $R_1$ is a hydrogen atom, or straight or branched C1-10 alkyl, in this case, $R_1$ optionally forms a bond with $L_1$, $L_2$, $Z_1$ or $Z_2$, to which $D_1$ and $D_2$ are not bound, s is an integer from 2 to 5 and t is an integer from 1 to 200, $L_1$ and $L_2$, which are optionally the same or different, are groups selected from the group consisting of a single bond, —$U_5$—, —$U_5$—$NR_2$—, —$U_5$—O—, —$U_5$—S—, —$U_5$—SS—, —$U_5$—$NR_2CO$—, —$U_5$—$CONR_2$—, —$U_5$—OCO—, —$U_5$—COO—, a group represented by the following chemical formula 7, and a group represented by the following chemical formula 8,

[Chem. 5]

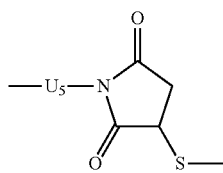
[Chemical Formula 7]

[Chem. 6]

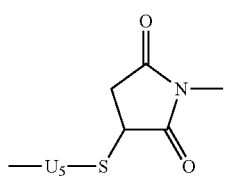
[Chemical Formula 8]

in this case, $U_5$ is substituted or unsubstituted straight or branched C1-10 alkylene, and $R_2$ is a hydrogen atom, or substituted or unsubstituted straight or branched C1-10 alkyl, the molar ratio of $p_1$ and $q_1$ ($p_1$:$q_1$) and the molar ratio of $p_2$ and $q_2$ ($p_2$:$q_2$) are 1:50 to 1:6,000, and the molar ratio of $p_1$ and $r_1$ ($p_1$:$r_1$) and the molar ratio of $p_2$ and $r_2$ ($p_2$:$r_2$) are 1:5 to 1:3,000.

2. The fluorescent hydrogel according to claim 1, which has a three-dimensional crosslinked structure.

3. A method for producing a fluorescent hydrogel, comprising (al) a step of polymerizing an aqueous solution comprising a fluorescent monomer represented by the following chemical formula 5, a monomer represented by the following chemical formula 9 and a polymerizable monomer comprising a (meth)acrylamide residue:

[Chem. 7]

[Chemical Formula 5]

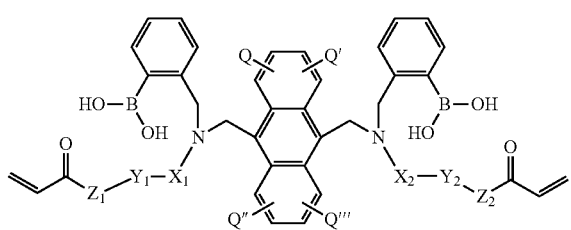

in the chemical formula 5, $X_1$ and $X_2$, which are optionally the same or different, are straight or branched $C_{1-30}$ alkylene which optionally comprises at least one substituent selected from the group consisting of —COO—, —OCO—, —$CH_2NR$—, —NR—, —NRCO—, —CONR—, —$SO_2NR$—, —$NRSO_2$—, —O—, —S—, —SS—, —NRCOO—, —OCONR— and —CO—, in this case, R is a hydrogen atom, or substituted or unsubstituted straight or branched C1-10 alkyl, $Z_1$ and $Z_2$, which are optionally the same or different, are —O— or —NR'—, in this case, R' is a hydrogen atom, or substituted or unsubstituted straight or branched C1-10 alkyl, Q, Q', Q" and Q"', which are optionally the same or different, are hydrogen atoms, hydroxy, substituted or unsubstituted straight or branched C1-10 alkyl, C2-11 acyl, substituted or unsubstituted straight or branched C1-10 alkoxy, halogen atom-containing groups, carboxyl, carboxylic acid ester, carboxylic acid amide, cyano, nitro, amino, or C1-10 alkylamino, and at least one of Q and Q', and Q" and Q"' optionally join together to form an aromatic ring or a heterocycle, $Y_1$ and $Y_2$, which are optionally the same or different, are divalent organic residues which are optionally substituted, or single bonds, in this case, at least one of $Y_1$ and $Y_2$ optionally contains a structure represented by the following chemical formula 3 or the following chemical formula 4,

[Chem. 8]

[Chemical Formula 3]

[Chem. 9]

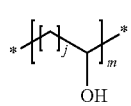
[Chemical Formula 4]

in the chemical formula 3 and the chemical formula 4, n is 2 to 5, j is 1 to 5, m is 1 to 200, and * represents a binding point,

[Chem. 10]

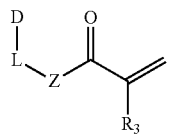
[Chemical Formula 9]

in the chemical formula 9, $R_3$ is a hydrogen atom or methyl, D is a group represented by the following chemical formula 6,

[Chem. 11]

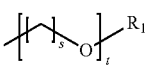
[Chemical Formula 6]

in the chemical formula 6, $R_1$ is a hydrogen atom, or straight or branched C1-10 alkyl, s is an integer from 2 to 5, and t is an integer from 1 to 200, Z, which is optionally the same or different, is —O— or —NR'—, in this case, R' is a hydrogen atom, or substituted or unsubstituted straight or branched C1-10 alkyl, L is a group selected from the group consisting of a single bond, —$U_5$—, —$U_5$—$NR_2$—, —$U_5$—O—, —$U_5$—S—, —$U_5$—SS—, —$U_5$—$NR_2$CO, —$U_5$—$CONR_2$—, —$U_5$—OCO—, —$U_5$—COO—, a group represented by the following chemical formula 7 and a group represented by the chemical formula 8,

[Chem. 12]

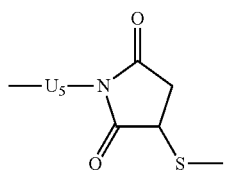

[Chemical Formula 7]

[Chem. 13]

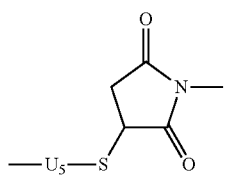

[Chemical Formula 8]

in this case, $U_5$ is substituted or unsubstituted straight or branched C1-10 alkylene, and $R_2$ is a hydrogen atom, or substituted or unsubstituted straight or branched C1-10 alkyl.

4. A method for producing a fluorescent hydrogel, comprising:
   (a2) a step of polymerizing an aqueous solution comprising a fluorescent monomer compound represented by the following chemical formula 5, a monomer represented by the following chemical formula 10 and a polymerizable monomer comprising a (meth)acrylamide residue; and
   (b) a step of reacting a compound represented by the following chemical formula 11:

[Chem. 14]

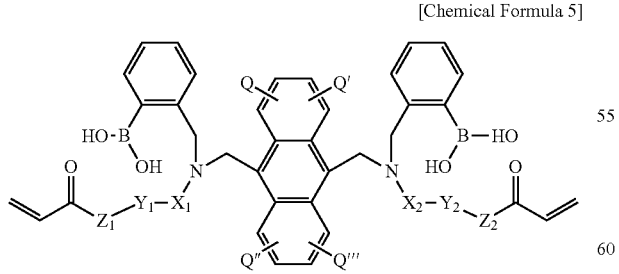

[Chemical Formula 5]

in the chemical formula 5, $X_1$ and $X_2$, which are optionally the same or different, are straight or branched C1-30 alkylene which optionally comprises at least one substituent selected from the group consisting of —COO—, —OCO—, —$CH_2$NR—, —NR—, —NRCO—, —CONR—, —$SO_2$NR—, —$NRSO_2$—, —O—, —S—, —SS—, —NRCOO—, —OCONR— and —CO—, in this case, R is a hydrogen atom, or substituted or unsubstituted straight or branched C1-10 alkyl, $Z_1$ and $Z_2$, which are optionally the same or different, are —O— or —NR'—, in this case, R' is a hydrogen atom, or substituted or unsubstituted straight or branched C1-10 alkyl, Q, Q', Q" and Q'", which are optionally the same or different, are hydrogen atoms, hydroxy, substituted or unsubstituted straight or branched C1-10 alkyl, C2-11 acyl, substituted or unsubstituted straight or branched C1-10 alkoxy, halogen atom-containing groups, carboxyl, carboxylic acid ester, carboxylic acid amide, cyano, nitro, amino, or C1-10 alkylamino, and at least one of Q and Q', and Q" and Q'" optionally join together to form an aromatic ring or a heterocycle, $Y_1$ and $Y_2$, which are optionally the same or different, are divalent organic residues which are optionally substituted, or single bonds, in this case, at least one of $Y_1$ and $Y_2$ optionally contains a structure represented by the following chemical formula 3 or the following chemical formula 4,

[Chem. 15]

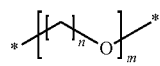

[Chemical Formula 3]

[Chem. 16]

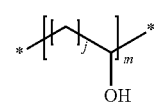

[Chemical Formula 4]

in the chemical formula 3 and the chemical formula 4, n is 2 to 5, j is 1 to 5, m is 1 to 200 and * represents a binding point,

[Chem. 17]

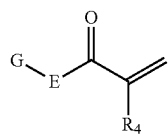

[Chemical Formula 10]

in the chemical formula 10, E is —O— or —NR'—, in this case, R' is a hydrogen atom, or substituted or unsubstituted C1-10 alkyl, G is substituted or unsubstituted straight or branched C1-10 alkyl which comprises a reactive functional group at its end, and $R_4$ is a hydrogen atom or methyl,

[Chem. 18]

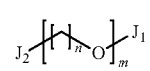

[Chemical Formula 11]

in the chemical formula 11, $J_1$ is a group comprising a hydrogen atom, substituted or unsubstituted straight or branched C1-10 alkyl, —$U_6$-halogen atom, —$U_6$—CHO, —$U_6$—SH, —$U_6$—$NH_2$, —$U_6$—$NHR_5$, —$U_6$—COON, —$U_6$—$COOR_5$, —$U_6$—O-para-toluenesulfonyl, —$U_6$-isothiocyanate, —$U_6$—OCO—$U_6$-isothiocyanate, —$U_6$-maleimide, —$U_6$—NHCO—$U_6$-maleimide, —$U_6$—CONH—$U_6$-maleimide, $OSO_2R_5$, —$U_6$—$OCOR_5$, —$U_6$—$(OR_5)_2$, —$U_6$—OCO-para-nitrophenyl, —$U_6$—OCO—$U_6$—COO—N-succinimide or —$U_6$—COO—N-succinimide, and $J_2$ is a group comprising —O—$U_6$-halogen atom, —O—$U_6$—CHO, —O—$U_6$—SH, —O—$U_6$—$NH_2$, —O—$U_6$—$NHR_5$, —O—$U_6$—COON, —O—$U_6$—$COOR_5$, —O—$U_6$—O-para-toluenesulfonyl, —O—$U_6$-isothiocyanate, —OCO—$U_6$-isothiocyanate, —O—$U_6$-maleimide, —O—$U_6$—NHCO—$U_6$-maleimide, —O—$U_6$—CONH—$U_6$-maleimide, —O—$U_6$—$OSO_2R_5$, —O—$U_6$—$OCOR_5$, —O—$U_6$—$(OR_5)_2$, —O—$U_6$—OCO-para-nitrophenyl, —OCO—$U_6$—COO—N-succinimide or —O—$U_6$—COO—N-succinimide, in this case, $U_6$ is substituted or unsubstituted straight or branched C1-10 alkylene, $R_5$ is a hydrogen atom, or substituted or unsubstituted straight or branched C1-10 alkyl, n is 2 to 5, and m is 1 to 200.

5. The method for producing a fluorescent hydrogel according to claim 3, wherein the step of polymerizing an aqueous solution is chemical polymerization of the aqueous solution using a radical polymerization initiator, photopolymerization of the aqueous solution using a photopolymerization initiator, or radiation polymerization of the aqueous solution by irradiating radiation.

6. An implantable sensor for measuring saccharides, comprising a fluorescent hydrogel according to claim 1.

7. An implantable sensor for measuring saccharides, which sensor has a means in which a fluorescent hydrogel according to claim 1 is implanted in a body and excitation light is irradiated from the inside of the body or the outside of the body to measure fluorescence emitted from the fluorescent hydrogel.

8. A sensor for measuring saccharides, which sensor has a means in which a fluorescent hydrogel according to claim 1 is put on at least a part of the path, along which body fluid is circulated, to measure fluorescence emitted from the fluorescent hydrogel.

9. An implantable sensor for measuring saccharides, comprising a fluorescent hydrogel obtained in the production method according to claim 3.

10. An implantable sensor for measuring saccharides, which sensor has a means in which a fluorescent hydrogel obtained in the production method according to claim 3 is implanted in a body and excitation light is irradiated from the inside of the body or the outside of the body to measure fluorescence emitted from the fluorescent hydrogel.

11. A sensor for measuring saccharides, which sensor has a means in which a fluorescent hydrogel obtained in the production method according to claim 3 is put on at least a part of the path, along which body fluid is circulated, to measure fluorescence emitted from the fluorescent hydrogel.

* * * * *